US008789826B2

(12) United States Patent
Giannuzzi

(10) Patent No.: US 8,789,826 B2
(45) Date of Patent: Jul. 29, 2014

(54) METHOD FOR EX-SITU LIFT-OUT SPECIMEN PREPARATION

(71) Applicant: EXpressLO LLC, Fort Myers, FL (US)

(72) Inventor: Lucille A. Giannuzzi, Fort Myers, FL (US)

(73) Assignee: EXpressLO LLC, Fort Myers, FL (US)

( * ) Notice: Subject to any disclaimer, the term of this patent is extended or adjusted under 35 U.S.C. 154(b) by 0 days.

(21) Appl. No.: 14/010,780

(22) Filed: Aug. 27, 2013

(65) Prior Publication Data

US 2013/0340936 A1 Dec. 26, 2013

Related U.S. Application Data

(62) Division of application No. 13/402,708, filed on Feb. 22, 2012, now Pat. No. 8,740,209.

(51) Int. Cl.
*B23Q 3/00* (2006.01)
*G21K 5/10* (2006.01)
*H01J 37/00* (2006.01)
*G01N 1/00* (2006.01)
*H01J 37/20* (2006.01)
*H01J 37/30* (2006.01)

(52) U.S. Cl.
CPC .............. *H01J 37/3002* (2013.01); *G01N 1/00* (2013.01); *H01J 2237/31745* (2013.01); *H01J 37/20* (2013.01); *H01J 2237/201* (2013.01)
USPC .................. 269/287; 250/492.21; 250/442.11

(58) Field of Classification Search
USPC ......................................................... 269/287
See application file for complete search history.

(56) References Cited

U.S. PATENT DOCUMENTS

| 4,307,507 | A | * | 12/1981 | Gray et al. ...................... 438/20 |
| 4,685,996 | A | * | 8/1987 | Busta et al. ..................... 438/20 |
| 4,916,002 | A | * | 4/1990 | Carver .......................... 428/139 |
| 4,939,364 | A | | 7/1990 | Ishitani et al. |
| 5,399,232 | A | * | 3/1995 | Albrecht et al. .................. 216/2 |
| 5,476,131 | A | * | 12/1995 | Hamilton et al. ................ 216/13 |
| 5,546,375 | A | * | 8/1996 | Shimada et al. .............. 369/126 |

(Continued)

OTHER PUBLICATIONS

L.A. Giannuzzi, J.L. Drown, S.R. Brown, R.B. Irwin, F.A. Stevie, "Focused Ion Beam Milling and Micromanipulation Lift-Out for Site Specific Cross-Section TEM Specimen Preparation," Mat. Res. Soc. Symp. Proc. vol. 480, Workshop on Specimen Preparation for TEM of Materials IV, (1997), Materials Research Society, p. 19-27.

(Continued)

*Primary Examiner* — Lee D Wilson
*Assistant Examiner* — Alvin Grant
(74) *Attorney, Agent, or Firm* — Marger, Johnson & McCollom, P.C.

(57) ABSTRACT

A method for mounting a specimen on a specimen carrier for milling in an ex-situ lift-out (EXLO) milling process is described where "cross-section" specimens, plan view specimens, or bulk specimens may be lifted-out for analysis. The method comprising positioning the specimen on a recessed surface within a specimen carrier top surface so that a region to be milled is centered about a carrier opening formed through the specimen carrier. Peripheral edges of the specimen are then wedged against inwardly sloping side walls framing the recessed surface. Finally, the specimen is mounted to the specimen carrier so that a path of a milling beam intersects the region to be milled and carrier opening.

19 Claims, 19 Drawing Sheets

(56) References Cited

U.S. PATENT DOCUMENTS

| | | | |
|---|---|---|---|
| 5,595,942 A * | 1/1997 | Albrecht et al. | 438/52 |
| 5,618,760 A * | 4/1997 | Soh et al. | 438/703 |
| 5,658,698 A * | 8/1997 | Yagi et al. | 430/11 |
| 5,666,190 A * | 9/1997 | Quate et al. | 355/71 |
| 5,742,377 A * | 4/1998 | Minne et al. | 355/71 |
| 5,866,021 A * | 2/1999 | Yagi et al. | 216/84 |
| 5,883,705 A * | 3/1999 | Minne et al. | 355/71 |
| 5,908,981 A * | 6/1999 | Atalar et al. | 73/105 |
| 5,923,637 A * | 7/1999 | Shimada et al. | 369/126 |
| 5,936,243 A * | 8/1999 | Gibson et al. | 850/26 |
| 5,959,957 A * | 9/1999 | Ikeda et al. | 369/127 |
| 5,994,160 A * | 11/1999 | Niedermann et al. | 438/53 |
| 5,994,750 A * | 11/1999 | Yagi | 257/415 |
| 6,000,947 A * | 12/1999 | Minne et al. | 438/759 |
| 6,011,261 A * | 1/2000 | Ikeda et al. | 850/32 |
| 6,016,686 A * | 1/2000 | Thundat | 73/23.2 |
| 6,056,887 A * | 5/2000 | Niedermann et al. | 216/2 |
| 6,075,585 A * | 6/2000 | Minne et al. | 355/71 |
| 6,118,124 A * | 9/2000 | Thundat et al. | 250/332 |
| 6,167,748 B1 * | 1/2001 | Britton et al. | 73/24.06 |
| 6,211,532 B1 * | 4/2001 | Yagi | 257/40 |
| 6,227,519 B1 * | 5/2001 | Yagi et al. | 249/114.1 |
| 6,232,150 B1 * | 5/2001 | Lin et al. | 438/119 |
| 6,289,717 B1 * | 9/2001 | Thundat et al. | 73/23.2 |
| 6,337,477 B1 * | 1/2002 | Shimada et al. | 250/216 |
| 6,400,166 B2 * | 6/2002 | Babson et al. | 324/755.05 |
| 6,420,722 B2 | 7/2002 | Moore et al. | |
| 6,436,853 B2 * | 8/2002 | Lin et al. | 438/800 |
| 6,570,170 B2 | 5/2003 | Moore | |
| 6,635,311 B1 * | 10/2003 | Mirkin et al. | 427/256 |
| 6,827,979 B2 * | 12/2004 | Mirkin et al. | 427/256 |
| 7,041,985 B1 | 5/2006 | Wang et al. | |
| 7,086,149 B2 * | 8/2006 | Eldridge et al. | 29/876 |
| 7,242,828 B2 * | 7/2007 | Oda et al. | 385/31 |
| 7,410,590 B2 * | 8/2008 | Van Schuylenbergh et al. | 216/11 |
| 7,523,650 B2 * | 4/2009 | Wang et al. | 73/105 |
| 7,541,219 B2 * | 6/2009 | Milligan et al. | 438/117 |
| 7,569,252 B2 * | 8/2009 | Mirkin et al. | 427/256 |
| 7,601,039 B2 * | 10/2009 | Eldridge et al. | 439/894 |
| 7,680,553 B2 * | 3/2010 | Popp | 700/108 |
| 7,737,045 B2 * | 6/2010 | Liu et al. | 438/738 |
| 7,737,709 B2 * | 6/2010 | Mathieu et al. | 324/750.16 |
| 7,861,315 B2 * | 12/2010 | Proksch et al. | 850/41 |
| 7,948,252 B2 * | 5/2011 | Grube et al. | 324/754.07 |
| 7,963,042 B2 * | 6/2011 | Keller | 30/350 |
| 7,985,081 B2 * | 7/2011 | Van Schuylenbergh et al. | 439/81 |
| 8,033,838 B2 * | 10/2011 | Eldridge et al. | 439/81 |
| 8,068,328 B2 * | 11/2011 | Raravikar et al. | 361/306.2 |
| 8,197,701 B2 * | 6/2012 | Carlisle et al. | 216/11 |
| 8,227,350 B2 * | 7/2012 | West et al. | 438/690 |
| 8,232,559 B2 * | 7/2012 | West et al. | 257/77 |
| 8,247,032 B2 * | 8/2012 | Mirkin et al. | 427/256 |
| 8,261,662 B1 * | 9/2012 | Shile et al. | 101/327 |
| 8,332,961 B2 * | 12/2012 | Bhaskaran et al. | 850/41 |
| 8,373,428 B2 * | 2/2013 | Eldridge et al. | 324/754.14 |
| 8,427,183 B2 * | 4/2013 | Mathieu et al. | 324/750.16 |
| 8,485,418 B2 * | 7/2013 | Eldridge et al. | 228/179.1 |
| 8,499,673 B2 * | 8/2013 | Keller | 83/701 |
| 2010/0032581 A1 | 2/2010 | Grosse et al. | |

OTHER PUBLICATIONS

L.A. Giannuzzi and F.A. Stevie, "A review of focused ion beam milling techniques for TEM Specimen preparation," Micron 30 (1999) 197-204.

F. A. Stevie, C. B. Vartuli, L. A. Giannuzzi, T. L. Shofner, S. R. Brown, B. Rossie, F. Hillion, R. H. Mills, M. Antonell, R. B. Irwin and B. M. Purcell, "Application of focused ion beam lift-out specimen preparation to TEM, SEM, STEM, AES and SIMS analysis," Surf. Interface Anal. 2001; 31: 345-351. DOI: 10.1002/sia.1063.

L.A. Giannuzzi, B.W. Kempshall, S.M. Schwarz, J.K. Lomness, B.I. Prenitzer, and F.A. Stevie, "FIB Lift-Out Specimen Preparation Techniques: Ex-situ and In-Situ Methods," in Introduction to Focused Ion Beams: Instrumentation, Theory, Techniques, and Practice, eds. Lucille A. Giannuzzi, and Fred A. Stevie, Springer, (2005), 201-228.

FEI Product Brochure, "TEMLink TEM Lamella Extraction Station," http://www.fei.com/uploadedfiles/Documents/Content/2008_05_TemLink_ds.pdf, May 2008, 2 Pages.

S.M. Schwarz and L.A. Giannuzzi, "FIB Specimen Preparation for STEM and EFTEM Tomography," Microscopy and Microanalysis, 10 (Suppl 2), (2004).

P.G. Kotula, L.N. Brewer, J.R. Michael, L.A. Giannuzzi, "Computed Tomographic Spectral Imaging: 3D STEM-EDS Spectral Imaging," Microsc Microanal 13(Suppl 2), 2007 1324CD.

M.K. Miller, K.F. Russell, G.B. Thompson,"Strategies for fabricating atom probe specimens with a dual beam FIB," Ultramicroscopy, vol. 102, Issue 4, Mar. 2005, pp. 287-298.

Stephen M. Schwarz, Brian W. Kempshall, Lucille A. Giannuzzi, and Molly R. McCartney, "Avoiding the Curtaining Effect: Backside Milling by FIB INLO," Microsc Microanal 9(Suppl 2), 2003 116-117, DOI: 10.1017/S1431927603441032.

M. R. McCartney, Jing Li, Partha Chakraborty, L. A. Giannuzzi, S. M. Schwarz, "Issues Affecting Quantitative Evaluation of Dopant Profiles Using Electron Holography," Microsc Microanal 9(Suppl 2), 2003, 776-777. DOI: 10.1017/S1431927603443882.

R. M. Langford, Y. Z. Huang, S. Lozano-Perez, J. M. Titchmarsh, and A. K. Petford-Long, "Preparation of site specific transmission electron microscopy plan-view specimens using a focused ion beam system," J. Vac. Sci. Technol. B 19(3), (2001) 755-758.

"Ex-Situ Lift-Out," video, http://www.kleindiek.com/exsitu-liftout.html, retrieved Mar. 6, 2012.

Patterson, R. J., Mayer, D., Weaver, L. and Phaneuf, M. W., "H-Bar Lift-Out" and "Plan-View Lift-Out": Robust, Re-thinnable FIB-TEM Preparation for Ex-Situ Cross-Sectional and Plan-View FIB Specimen Preparation, Microscopy and Microanalysis, Aug. 2002, vol. 8, pp. 566-567.

Phaneuf, M. W. and Patterson, R. J., Site-specific TEM Specimen Preparation of Grain Boundary Corrosion in Nickel-Based Alloys Using the FIB "Plan-View Lift-Out" Technique, Microscopy and Microanalysis, Aug. 2002, vol. 8, pp. 1266-1267.

Rossie, B. B., Shofner, T. L., Brown, S. R., Anderson, S. D., Jamison, M. M., and Stevie, F. A., A Method for Thinning FIB Prepared TEM Specimens After Lift-Out, Microscopy and Microanalysis, 2001, vol. 7, p. 940-941.

\* cited by examiner

METHOD FOR EX-SITU LIFT-OUT SPECIMEN PREPARATION

CROSS-REFERENCE TO RELATED PATENT APPLICATION

This application is a Divisional of U.S. Ser. No. 13/402,708, filed on Feb. 22, 2012, now pending, which is hereby incorporated by reference in its entirety.

BACKGROUND OF THE INVENTION

1. Field of the Invention

The present invention relates to a method and apparatus for positioning a specimen on a specimen carrier (e.g., 3 mm grid or post) such that the specimen may be further thinned with e.g., FIB milling, broad ion beam milling, or laser ablation. In addition, this method and apparatus allows for positioning of the specimen to reduce or eliminate ion milling or laser ablation curtaining artifacts.

2. Description of the Related Art

The ex-situ lift-out (EXLO) method is a well-known technique that is typically used to prepare specimens for subsequent transmission electron microscope (TEM) or other analysis using focused ion beam (FIB) milling routines. In this method, specimens are completely FIB milled free inside of a charged particle vacuum environment and then the specimen is manipulated to a carbon or formvar coated TEM grid using a microscope and micromanipulator system in ambient conditions outside of the FIB. The advantages to the EXLO method are: (i) little or no initial specimen preparation is needed, (ii) it is site specific, (iii) it is fast, and (iv) it has a high success rate. The primary disadvantages to the EXLO technique are: (i) it is difficult and/or impossible to further thin the specimen, (ii) it is difficult and/or impossible to perform back-side milling on a specimen to avoid curtaining artifacts, and (iii) the carbon or formvar support film may inhibit certain analyses or cleaning operations.

Manipulation in ambient conditions of the specimen to the grid may be performed by different probing methods. One conventional method utilizes static attraction by touching a solid glass needle to the specimen for transfer to a carbon or formvar coated grid. In another method, a needle can be dipped in glue to adhere the specimen to the probe for transfer to a grid which also contains glue. In yet another method of specimen manipulation technique, a suction or vacuum pulled through a hollow needle can be used to capture the specimen for manipulation to a carbon or formvar grid. Probes with a variety of grippers may also be used to transfer the specimen to a grid.

FIB milling or laser ablation may be used to create a cross sectioned surface for subsequent site specific analytical characterization. It is well known that material removal rates are dependent on dose, incidence angle, crystal orientation, and material composition. A ubiquitous cross sectioning artifact known colloquially as "curtaining" or the "waterfall effect" consists of local roughness and thickness variation of the surface, and is a direct result of differences in removal rates that may be inherent to the specimen composition or geometry. Curtaining is so named due to the appearance and observation of lines of differential milling that resemble theater curtains which form on the milled surface parallel to the beam direction. The presence and observation of these lines is a direct indication of an uneven and rough milled surface.

Surface roughness and irregular specimen thickness can be problematic for many electron microscopy and other techniques used to analyze the FIB milled surface. As an example, conventionally prepared FIB milled specimens of semiconductor gate structures will yield curtaining artifacts that create thickness changes in the substrate which render 2D dopant analysis via electron holography useless.

Accordingly, the need remains for a method to eliminate such irregularities in the surface of specimens so that they can be properly analyzed.

SUMMARY OF THE INVENTION

In order to solve the issues associated with the impossibility and/or difficulty of re-thinning EXLO specimens and FIB milled curtaining artifacts, the present invention provides a method of EXLO manipulation to a carrier (e.g., TEM grid or post) design which allows support for the specimen without the need for a carbon or formvar coating film. In addition, asymmetric FIB milling of the specimen allows for identification of the "top" or "bottom" of the specimen such that the specimen position may be manipulated to the grid in any desired orientation.

In one aspect of the invention, a specimen carrier for use with an ex-situ lift-out (EXLO) milling process includes a carrier top surface having at least one specimen support area. The carrier further includes an aperture formed through the specimen carrier top surface within the specimen support area and having a wider upper end and a narrower lower end. The aperture includes a first opening adjacent to the top surface and a recessed opening aligned with said first opening. The first opening is bounded by opposed sidewalls in spaced-apart orientation that are inwardly inclined from the wider upper end to the narrower lower end. The recessed opening is bounded by opposed sidewalls in spaced-apart orientation narrower than the opposed sidewalls of the first opening to thereby define a resting surface between the sidewalls of the first opening and the sidewalls of the recessed opening. Thus configured, the specimen carrier enables a specimen to sit over the recessed opening on the resting surface and below the carrier top surface and wedged between the first opening opposed sidewalls so that a region of interest to be milled is centered about the recessed opening.

In another aspect of the invention, a specimen carrier for use with an ex-situ lift-out (EXLO) milling process includes a carrier top surface having at least one specimen support area and at least one aperture formed through the specimen carrier top surface. The aperture, formed within the specimen support area, includes a first opening having an open wider upper end and a narrower lower end. The first opening is bounded by opposed sidewalls in spaced-apart orientation that are inwardly inclined from the wider upper end to the narrower lower end. The aperture is configured to enable a specimen to sit over the opening and can be wedged between the first opening opposed sidewalls so that a region of interest to be milled is centered about the open end of the opening. Specimens so mounted can then be re-thinned via charged particle instruments such as focused ion beam (FIB) milling, broad beam ion milling, or via laser ablation.

Further described is a method for mounting a specimen on a specimen carrier for milling in an ex-situ lift-out (EXLO) milling process where "cross-section" specimens, plan view specimens, or bulk specimens may be lifted-out for analysis. The method comprising positioning the specimen on a recessed surface within a specimen carrier top surface so that a region to be milled is centered about a carrier opening formed through the specimen carrier. Peripheral edges of the specimen are then wedged against inwardly sloping side walls framing the recessed surface. Finally, the specimen is mounted to the specimen carrier so that a path of a milling beam intersects the region to be milled and carrier opening.

The specimen is placed flat onto the carrier and attached via the large surface tension forces, but may also be adhered using glue, epoxy, an adhesive, or by site specific ion beam or electron beam induced chemical vapor deposition. EXLO manipulation of the specimen may be performed via static attraction, suction, adhesive on the tip to grab the specimen, via a gripper-type end-effector, or other manipulating device. The specimen may be directly analyzed after manipulation or may be further processed or sequentially processed/analyzed.

The foregoing and other objects, features and advantages of the invention will become more readily apparent from the following detailed description of a preferred embodiment of the invention that proceeds with reference to the accompanying drawings.

DETAILED DESCRIPTION

This application describes embodiments in which a site specific specimen is processed in a charge partial instrument (e.g., FIB) or via laser ablation and then lift-out is performed outside (i.e., ex-situ) of such instrument without the need for a carbon or formvar support film such that the specimen may be directly analyzed by e.g., transmission electron microscopy (TEM), scanning electron microscopy (SEM), electron tomography, atom probe tomography (APT), or other characterization method. The novelty of this invention is that the specimen may be re-thinned if necessary using FIB, broad ion milling, laser ablation, or similar (collectively "milling"). In addition, this EXLO procedure is performed in a manner whereby the specimen positioning for re-thinning via FIB (or laser) may reduce or eliminate curtaining artifacts.

Backside FIB milling techniques of semiconductor gate specimens can reduce curtaining artifacts of the substrate for electron holography analysis. This present invention describes a specimen carrier and FIB milling steps and positioning of a specimen via EXLO that readily allows for backside FIB milling and a reduction or elimination of curtaining artifacts in the substrate.

Once the specimen is manipulated to the carrier, it can be directly analyzed by any number of analytical methods or taken back into the FIB or other material removal procedure (e.g., laser) for additional thinning of the specimen prior to analysis. After the specimen is manipulated to the carrier, it can be additionally secured if desired using either electron beam chemical vapor deposition and/or ion beam chemical vapor deposition methods prior to re-thinning.

Plan view specimens may be prepared by EXLO. However, this method typically requires a 2-step lift-out process. The application described herein negates the need for a 2-step lift-out process so that plan view specimens can be directly prepared for analysis.

Figure 1:
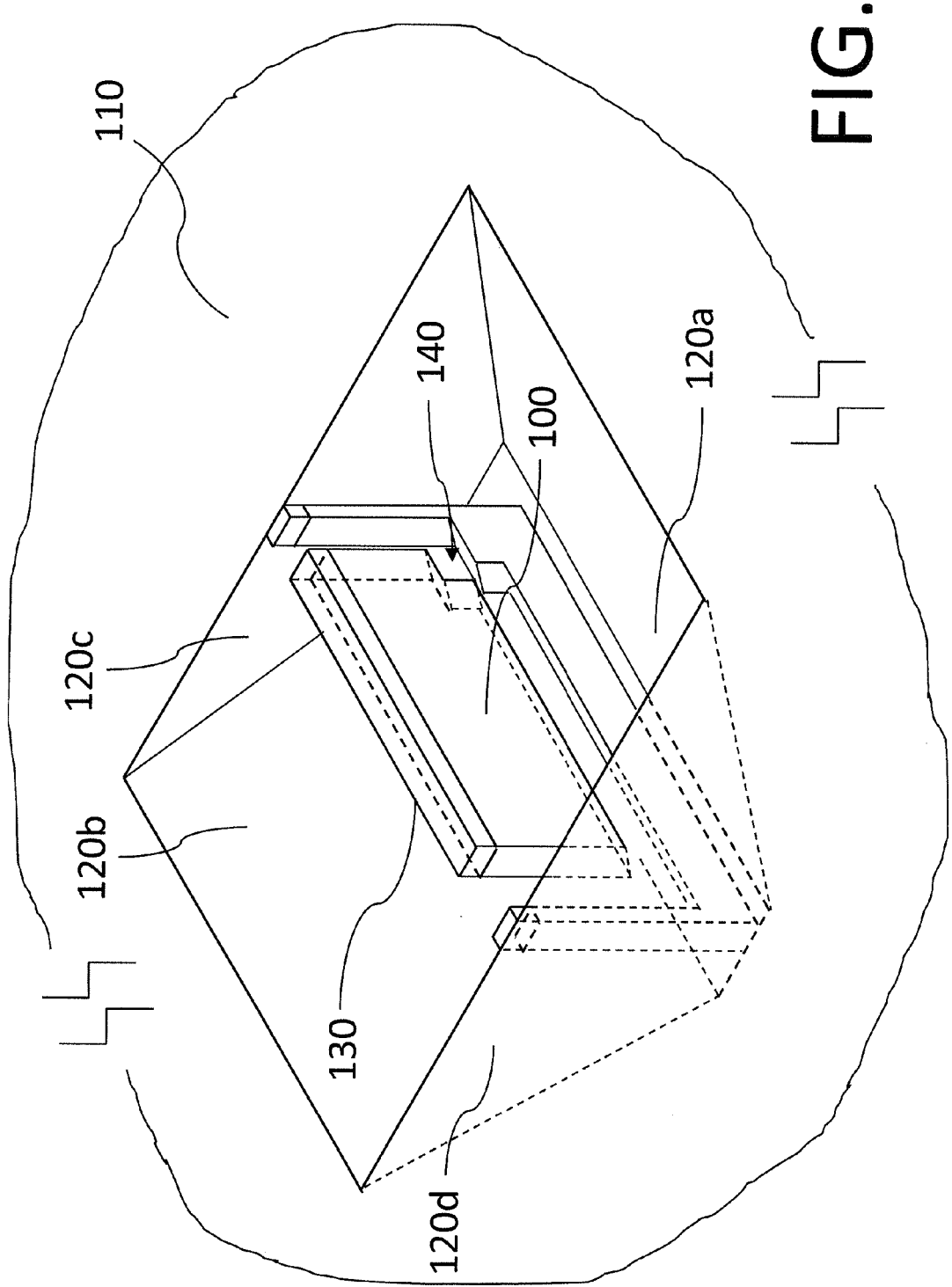
FIG. 1 is a perspective view of a specimen taken from a sample to be analyzed where the specimen includes an asymmetric cut to uniquely identify an orientation of the specimen.

FIG. 1 shows a "cross-section" EXLO specimen 100 FIB milled from the target surface 110. The completely FIB milled free EXLO specimen 100 sits inside of FIB milled trenches 120a, 120b, 120c, and 120d. The specimen 100 may be denoted by a protective layer 130, which may be deposited inside of a dual platform FIB/SEM instrument. This layer 130 may be formed of platinum, carbon, tungsten or similar and is used to mark the region of interest and protect the underlying surface from spurious milling.

In a preferred implementation of the invention, the EXLO specimen 100 is asymmetrically shaped or a layer may be deposited to indicate an orientation of the specimen on a carrier such as the ones described below. In one aspect, the protective layer 130 formed on the top of the sample can be made thick enough to be used as an indicator for positioning the sample in either an "upright" or "backside" orientation. In another aspect, and as shown in FIG. 1, the specimen may be FIB milled free using asymmetric FIB release milled cuts 140 where the shape of the milled cuts on the one side of the specimen are different than on the other side. The asymmetric cuts help to denote the orientation of the specimen. In this example, the milled free cut on the left side of specimen 100 is a single vertical cut, whereas the cut on the right side of specimen 100 is "stair-stepped." Another example of an asymmetric cut would be to have the left side cut be perfectly vertical and the right side cut be angled from the top to bottom of specimen 100. Once specimen 100 is completely FIB milled free, the target 110 is removed from the FIB and the specimen 100 is removed from its trenches via ambient or "ex-situ" micromanipulation.

Figure 2:
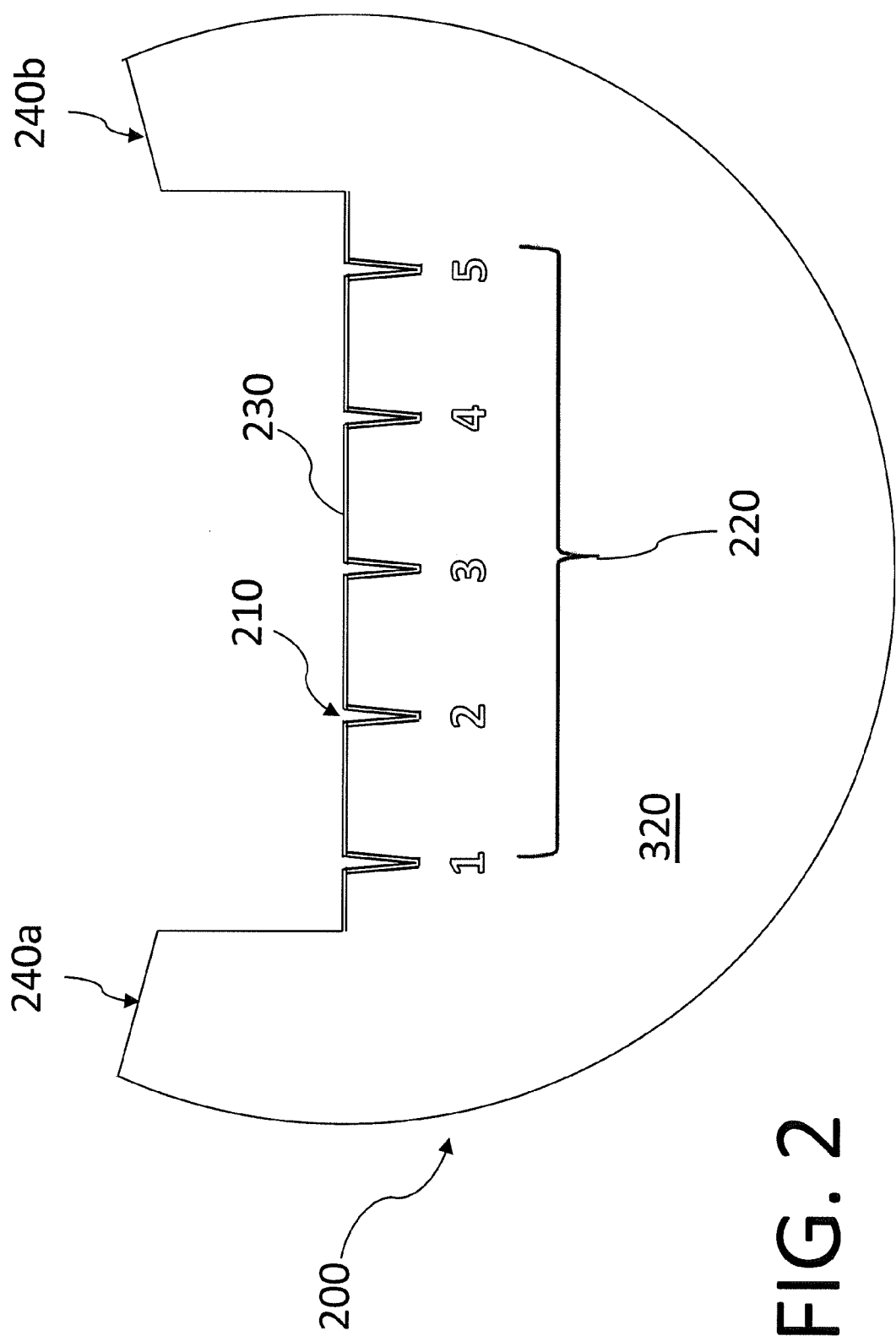
FIG. 2 shows a plan view of a specimen carrier configured according to a first embodiment of the invention.

FIG. 2 shows an examplary specimen carrier (e.g., TEM grid) 200 configured according to teachings of a first embodiment of the invention. The carrier 200 may be produced from copper, nickel, titanium, molybdenum, silicon, or similar. The carrier 200 may be about 3 mm in diameter, and about 5-100 micrometers or more in thickness. Carrier 200 provides a flat surface for the manipulating and mounting of the EXLO specimen so that the specimen can be milled and/or inspected. In one aspect, the carrier is configured in a partial disc-shape with wings 240a, 240b framing each side of a specimen mounting area and extending above the front or facing surface 230. Within the specimen mounting area are located one or more (five are shown in the figure) carrier specimen area cut outs or apertures 210 where the center region is devoid of both carrier material and any carbon/formvar film support. The five specimen support regions shown in the embodiment are numbered with indicia 220 for identification purposes so that multiple EXLO specimens can be manipulated and mounted to the same grid carrier 200. The configuration shown allows for manipulation of an EXLO sample to a flat surface while exposing the region of interest on the specimen through a V-shaped slot 210. The V-shape slot allows for different specimen dimensions to be manipulated anywhere along the "V" length.

Figure 3:
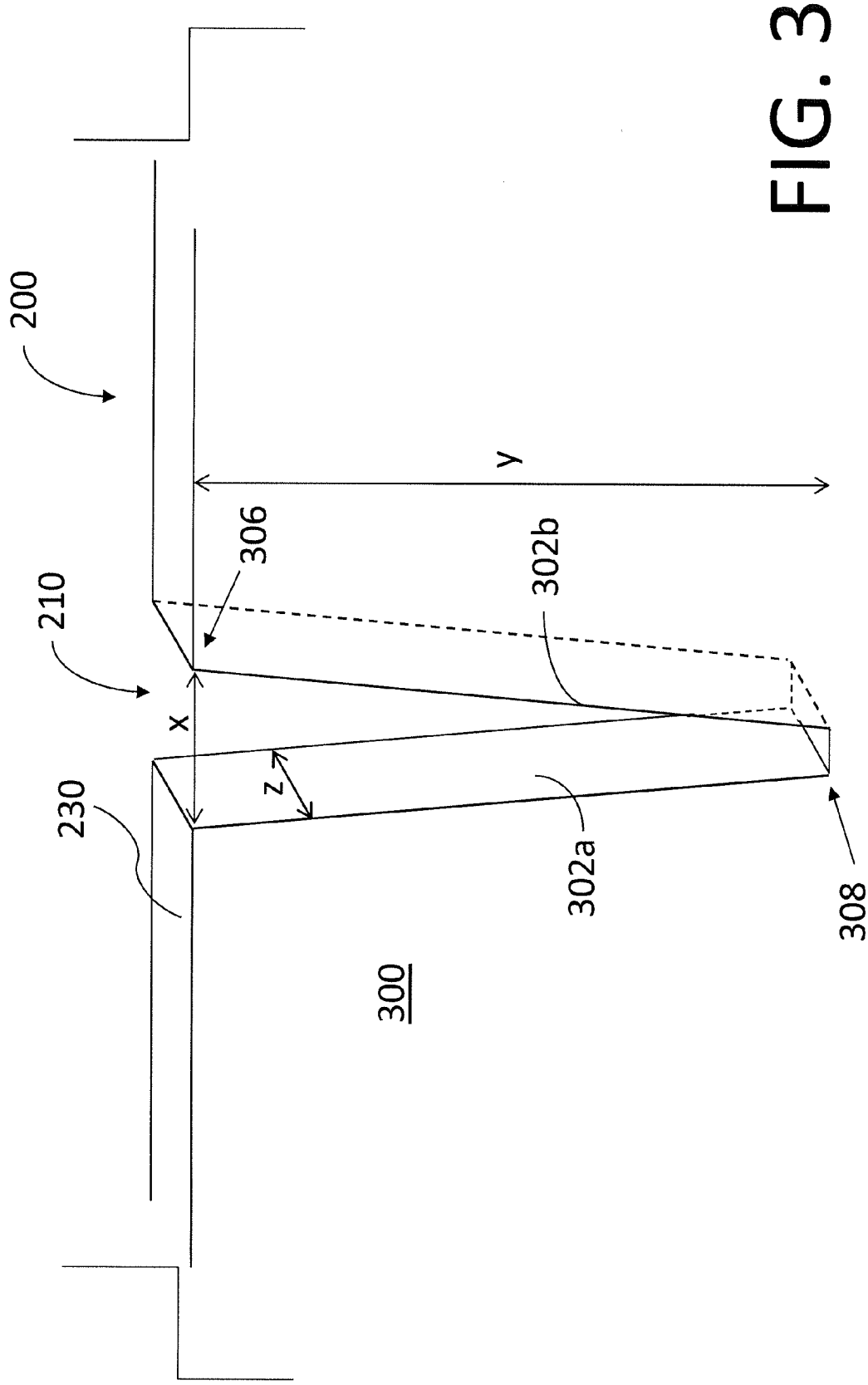
FIG. 3 shows a perspective view of a single specimen support area in the specimen carrier of FIG. 2, 9, or 10 configured according to an alternative embodiment of the invention.

FIG. 3 is a perspective view showing a specimen carrier for use with an ex-situ lift-out (EXLO) milling process. The carrier comprises a carrier body 200 having a facing surface 230 and opposed front 300 and back sides. The carrier includes at least one specimen mounting area defined along the facing surface comprising an aperture 210 formed completely through the carrier body between opposed front and back sides and bounded by opposing aperture sidewalls 302a, and 302b. Sidewalls 302a, 302b span between an open upper end 306 along the facing surface 230 of the carrier body and taper to a narrow lower end 308. In use, the specimen carrier is configured to enable a specimen to sit over or within the aperture between the opposed sidewalls so that a region of interest to be milled is centered about the aperture 210.

The opening dimension "x" at upper end 304 may be similar to that of a typical EXLO specimen (e.g., 5-100 micrometers or more). The sidewalls 302a, 302b of the opening are slanted along the height of opening "y" to accommodate smaller specimens such that the EXLO specimen may be positioned anywhere along this opening. Although a straight line slant for sidewalls 302a, 302b is shown, it is understand that many configurations are possible that cause a decrease in width, such as inwardly curved sidewalls, step-function sidewalls, etc. The height "y" of the aperture 210 may extend for say 50-200 micrometers or more. The total thickness "z" of the grid carrier is approximately between 5-100 micrometers or more.

Figure 4:
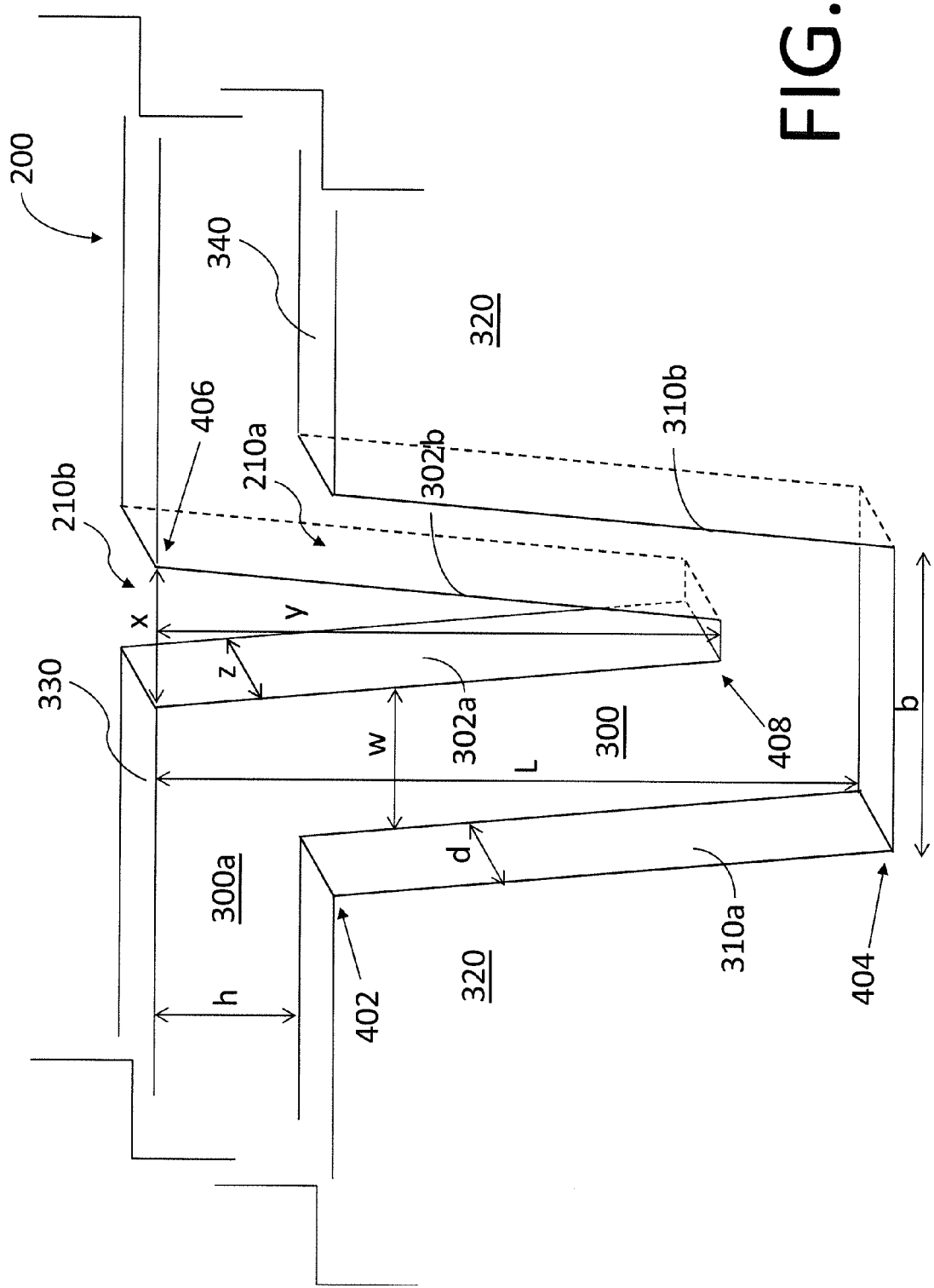
FIG. 4 shows a perspective view of a single specimen support area in the specimen carrier of FIG. 2, 9 or 10 configured according to the preferred embodiment of the invention.

FIG. 4 illustrates a principal embodiment of the specimen support area 210 of grid carrier 200. In this aspect of the invention, the specimen carrier 200 for use with an ex-situ lift-out (EXLO) milling process includes a carrier outer surface 320 having at least one specimen support area. The carrier further includes an aperture 210 formed through the specimen carrier outer surface 320 within the specimen support area and having a wider upper end and a narrower lower end. The aperture includes a first opening 210a, adjacent to the outer surface 320, and a recessed opening 210b, aligned with said first opening 210a. The first opening is bounded by opposed sidewalls 310a and 310b in spaced-apart orientation that are inwardly inclined from the wider upper 402 end to the narrower lower end 404. The recessed opening 210b is bounded by opposed sidewalls 302a, 302b in spaced-apart orientation, with a wider upper end 406 and narrower lower end 404, that are each inward of the opposed sidewalls of the first opening 210a to thereby define a resting surface 300 between the sidewalls 310a, 310b of the first opening and the sidewalls 302a, 302b of the recessed opening 210b in a plane that is recessed from carrier outer surface 320. Thus configured, the specimen carrier enables a specimen to sit over the recessed opening on the resting surface and below the carrier outer surface 320 and wedged between the first opening opposed sidewalls 310a, 310b so that a region of interest to be milled is centered about the recessed opening 210b. The upper end 340 of outer surface 320 is recessed from front or leading surface 330 to thereby define a contiguous portion 300a of the resting surface defined above the upper end 402 of the first opening and within the same plane as the resting surface 300.

The recessed opening dimension "x" may be similar to that of a typical EXLO specimen (e.g., 5-100 micrometers or more). The sidewalls 302a, 302b of the opening are slanted along the length of opening "y" to accommodate smaller specimens such that the EXLO specimen may be positioned anywhere along this opening. The dimension "y" may extend for say 50-200 micrometers or more. The opening 210—formed of first opening 210a and recessed opening 210b—contains a recessed edge having a depth of dimension "d" such that the specimen may be protected and sit below the outer surface 320 of the grid carrier 200 and onto surface 300. The depth "d" may be say ~5-50 micrometers or more. The total thickness of the grid carrier is the sum of dimensions "z" and "d" and this total thickness may be say 5-100 micrometers or more. Surface 340 may be recessed from surface 330 by a height "h" and width "w", where "h" and "w" may be on the order or 5-50 micrometers or more.

The principal embodiment, with recessed resting surface 300, allows for manipulation of an EXLO sample to a flat surface while exposing the region on interest on the specimen through a V-shaped slot 210b. The V-shape slot 210b allows for different specimen dimensions to be manipulated anywhere along the "V" length. The recessed region protects the specimen from touching any other surface. The V-shape of the recessed area may be used to wedge and secure the specimen in place for additional support.

Figure 5:
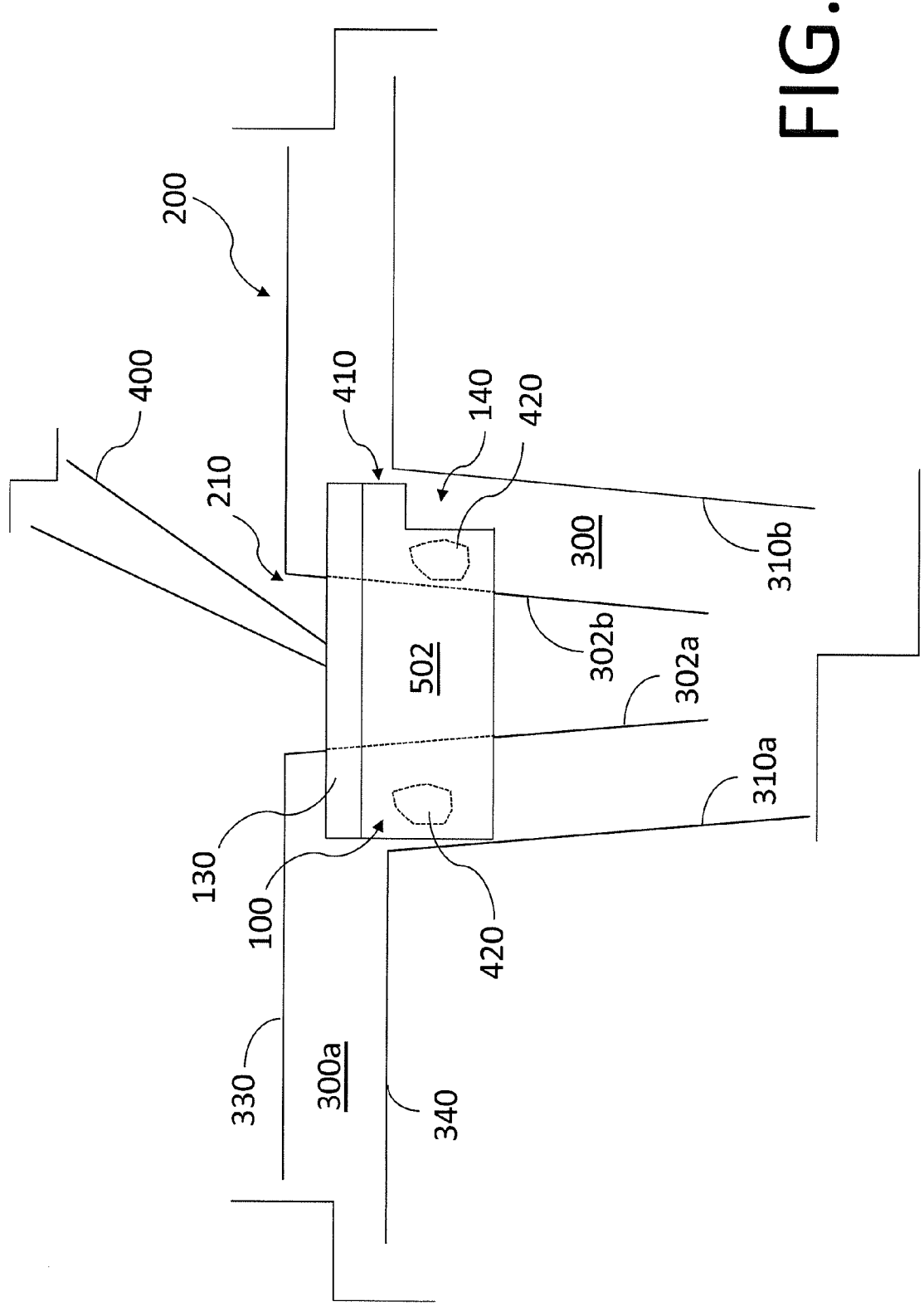
FIG. 5 shows a plan view of the specimen support area of FIG. 4 with the EXLO specimen of FIG. 1 mounted thereon in an upright orientation according to one embodiment of the invention.

FIG. 5 illustrates the manipulation of an EXLO specimen 410 onto the newly designed carrier apparatus 200 in an upright orientation. Note that manipulation is performed by a tool, such as ex-situ micromanipulator 400, in ambient conditions outside of the FIB/SEM apparatus (not shown). The specimen 100 is shown secured to the carrier 200 via surface tension forces. However, glue, adhesive or epoxy 420 may be used to additionally secure the specimen to the carrier 200 and within grid carrier opening 210. As shown, the region of interested 520 is centered about the carrier opening 210. The specimen 100 is positioned onto surface 300 and may be wedged or placed against the edges 310a, 310b spanning surface 300 for additional support. In FIG. 5 the specimen 100 is manipulated in an upright orientation where the asymmetric cutout 140 formed in the specimen is located at a lower right end, thus making its mounted orientation obvious. If flipped over to a backside orientation, the cutout 140 would be located on the lower left side or upper right side (see, e.g., FIG. 6).

Figure 6:
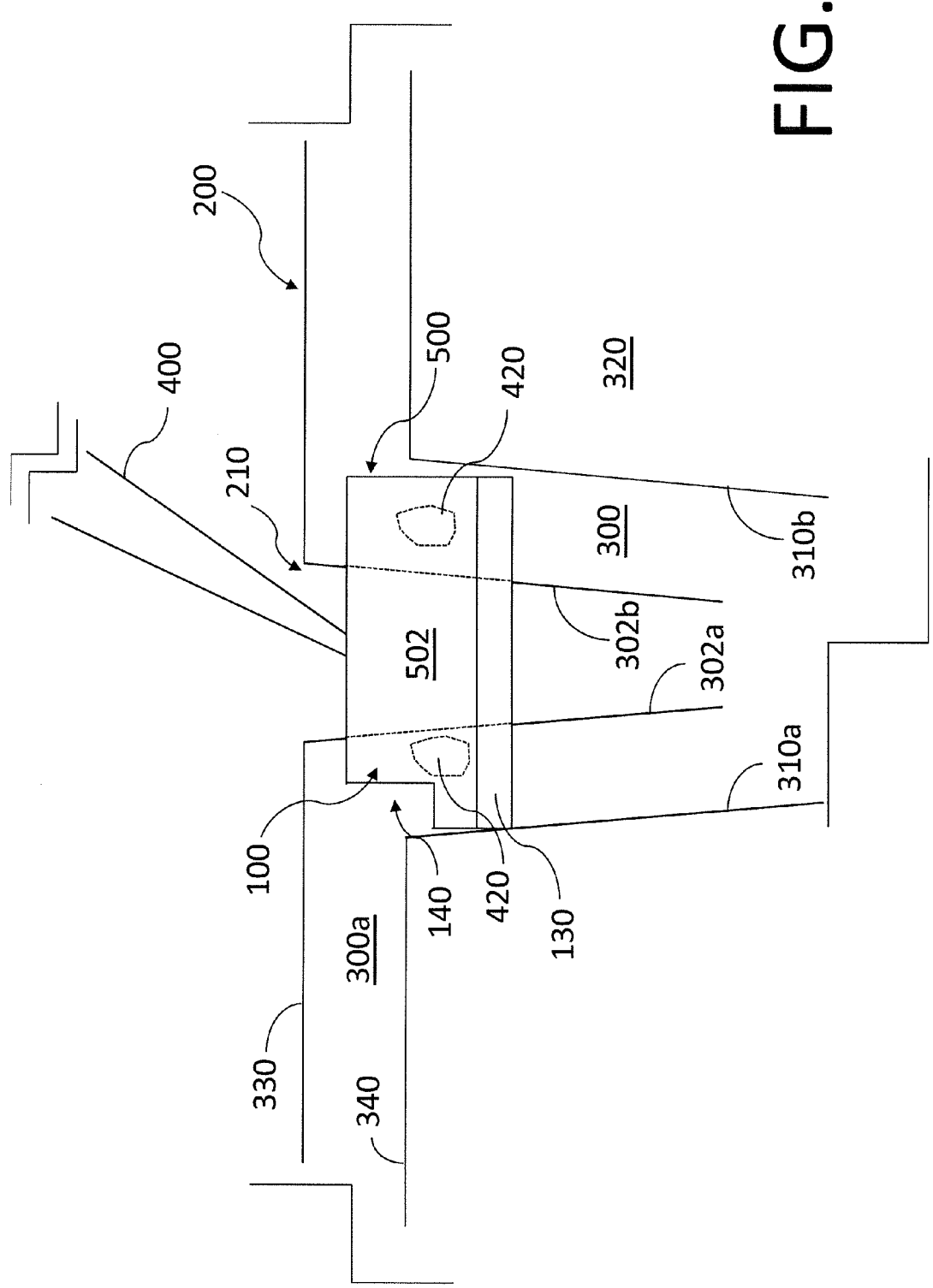
FIG. 6 shows a plan view of the specimen support area of FIG. 4 with the EXLO specimen of FIG. 1 mounted thereon in a backside orientation according to one embodiment of the invention.

FIG. 6 shows the manipulation by a tool, such as ex-situ micromanipulator 400, of an EXLO specimen 100 onto the newly designed carrier apparatus 200 whose region of interested 502 is centered about the carrier opening 210. The specimen 100 is positioned onto surface 300 and may be wedged or placed against the sidewalls 310a, 310b defining surface 300 (and 300a) for additional support. In FIG. 6 the specimen 100 is manipulated in a backside orientation 500 made obvious by the fact that asymmetric cut 140 is now shown in the upper left side of specimen 100. The carrier may be rotation with respect to the specimen or the specimen may be rotated/manipulated relative to the carrier to present the backside "up." The specimen is secured to the carrier via surface tension forces. The use of a glue, epoxy, or adhesive 420 may also be used to adhere the specimen 100 to the carrier 200 and the grid carrier opening 210 on surface 300.

Figure 7:
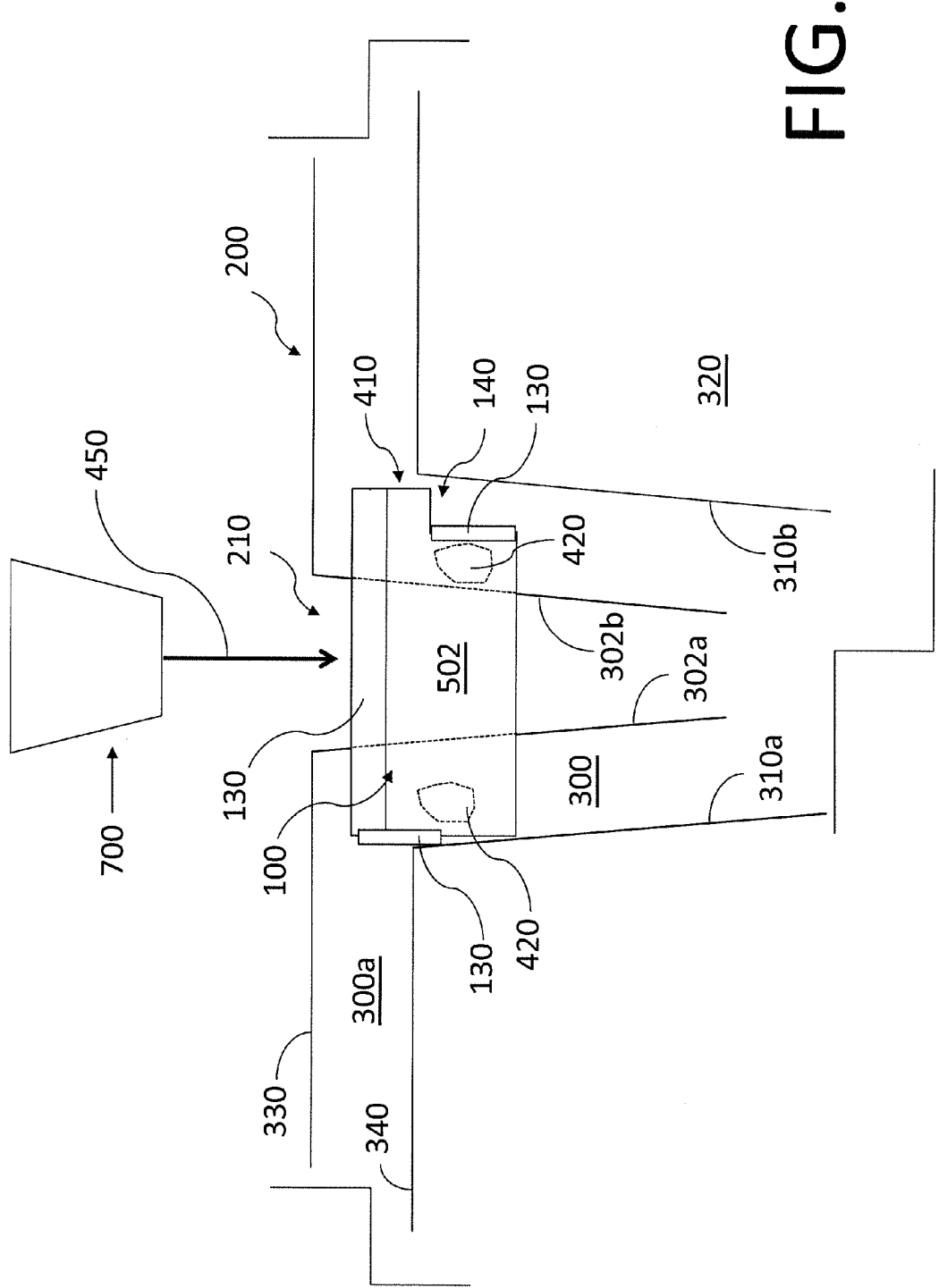
FIG. 7 shows a plan view of the specimen in the orientation shown in FIG. 5 attached to the specimen support area using an additional deposition layer and the ability to further process the specimen with a FIB or other milling/ablation beam according to yet another aspect of the invention.

FIG. 7 shows a glued 420 upright oriented EXLO specimen 100, 410 after manipulation onto the carrier 200 and the carrier opening 210 onto recessed mounting surfaces 300, 300a. The specimen may be directly analyzed at this point or may be put back into a FIB/SEM or similar where an additional layer may be deposited 130 on one or more sides to further secure and protect the specimen 100. The specimen may be further thinned by a FIB or laser tool 700 projected along path 450 or may be processed alternatively by a thinning beam (e.g., FIB or laser) and an imaging beam (e.g., FIB 450 or SEM, TEM etc. (not shown)) for 3D tomography from the direction defined by the exposed side of the carrier—i.e. via the open end of aperture 210.

Figure 8:
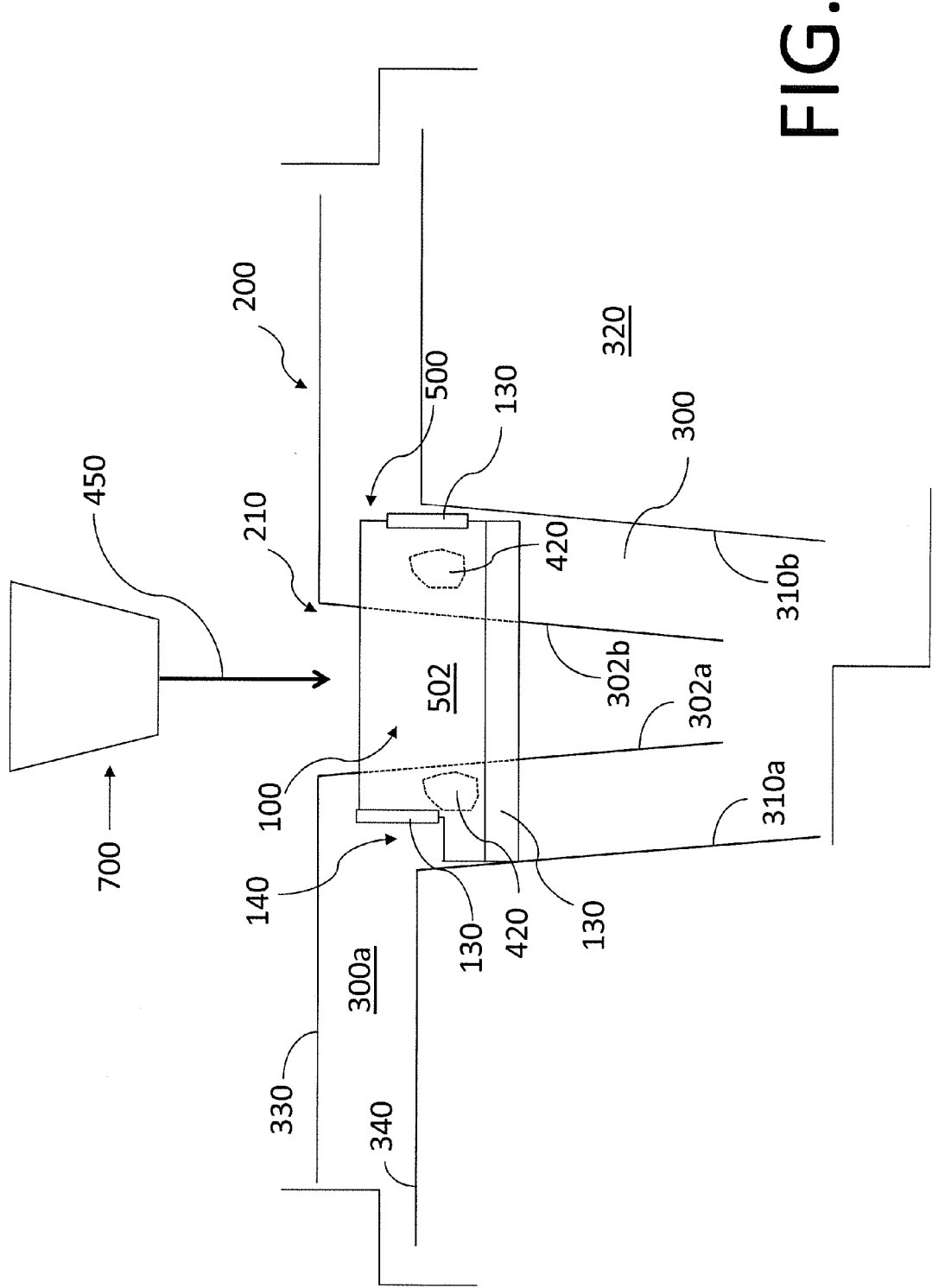
FIG. 8 shows a plan view of the specimen in the orientation shown in FIG. 6 attached to the specimen support area using an additional deposition layer and the ability to further process the specimen with a FIB or other milling/ablation beam according to yet another aspect of the invention.

FIG. 8 shows a glued 420 backside orientated EXLO specimen 100, 500 after manipulation onto the carrier 200 and the carrier opening 210 onto surfaces 300, 300a. The specimen may be directly analyzed at this point or may be put back into a FIB/SEM where an additional ion beam or electron beam deposition layer 130 may be deposited on one or more sides to further secure the specimen 100. An additional deposition layer (not shown) may be added to the top of the specimen (now, its "backside"). The focused ion beam tool 700 projected along path 450 may be used to further thin/process the specimen thickness from the direction defined by the exposed side of the carrier.

Figure 9:
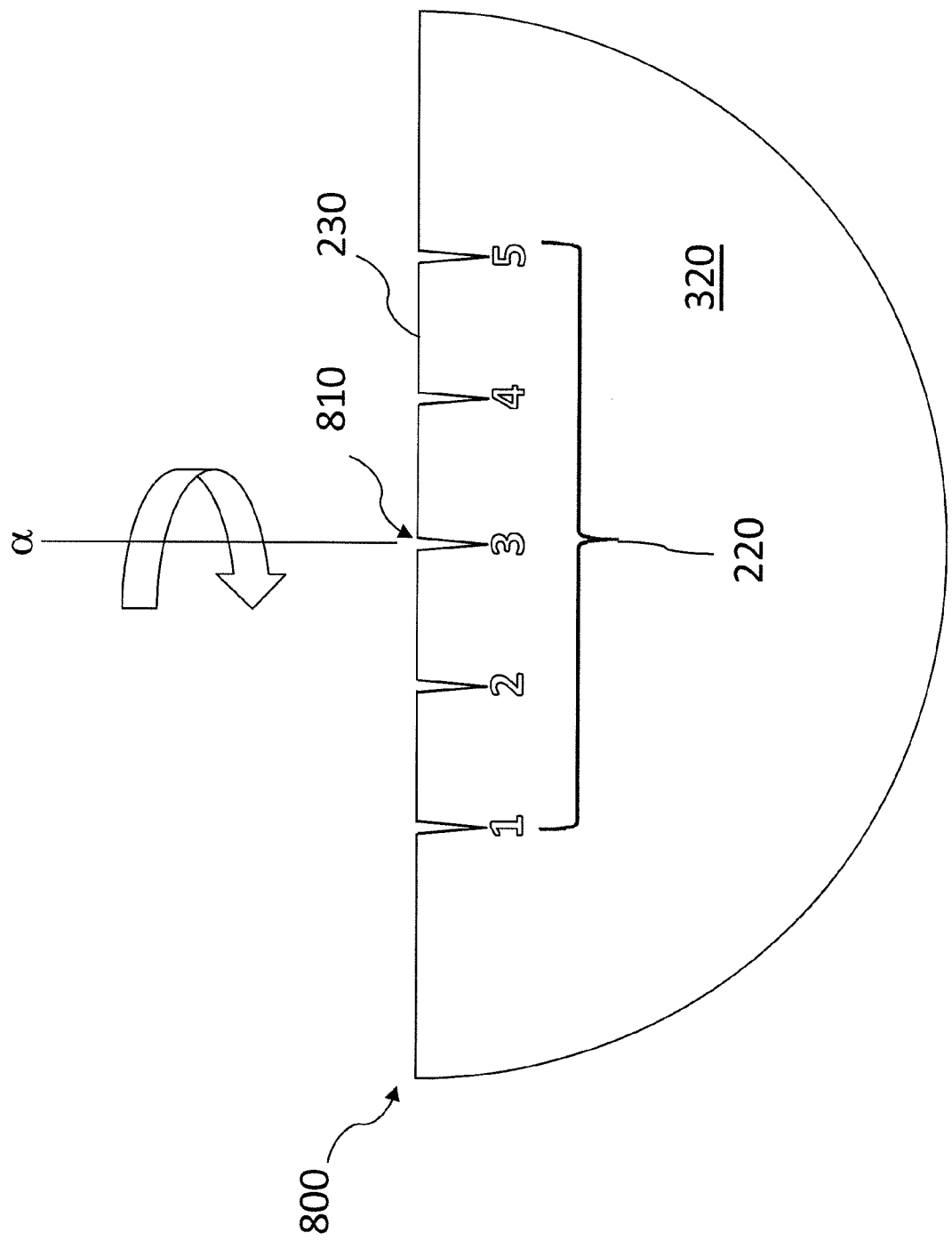
FIG. 9 shows a plan view of a specimen carrier configured using a low profile design according to a second embodiment of the invention.

FIG. 9 shows a low profile grid carrier 800 whose openings 810 and specimen support area are similar to that of FIG. 2 and FIG. 3 ((210) and its details). The low profile grid carrier allows for unobstructed view of a single specimen during rotation about axis α for e.g., electron tomography analysis. The low profile grid carrier design 800 enables an unobstructed view of the specimen during full grid rotation/tilt after the specimen 100 has been manipulated to the carrier.

Figure 10:
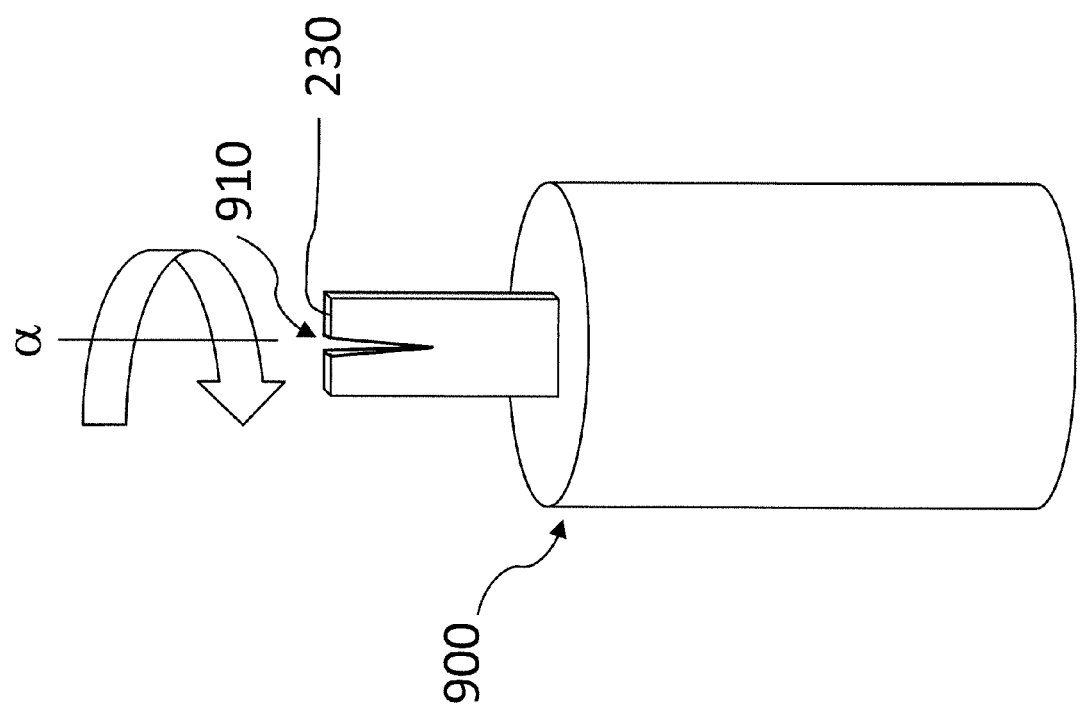
FIG. 10 shows perspective view of a specimen carrier configured using a low profile post carrier design according to a third embodiment of the invention.

FIG. 10 shows a low profile grid post-shaped carrier 900 whose opening 910 and specimen support area are similar to that of FIG. 2 and FIG. 3 ((210) and its details). The low profile grid carrier allows for unobstructed view of the specimen during rotation about axis a for e.g., full grid rotation/tilt electron tomography analysis.

Figure 11:
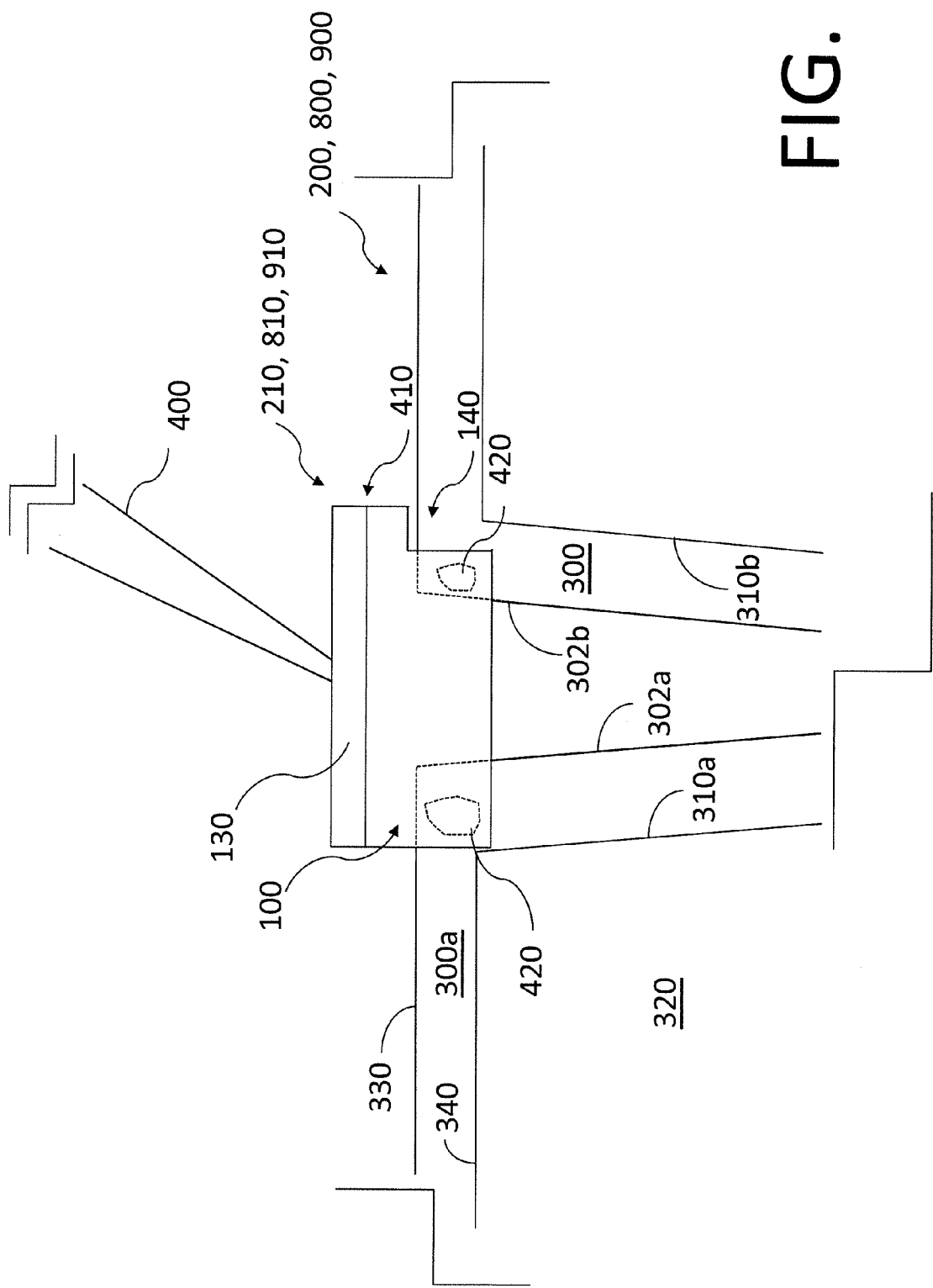
FIG. 11 shows a plan view of the specimen support area of FIG. 4 with the EXLO specimen of FIG. 1 manipulated to an upright orientation above a facing surface of the grid.

FIG. 11 shows the manipulation, such as using ex-situ micromanipulator 400, of an EXLO specimen 100 onto a carrier apparatus (200, 800, or 900) whose region of interested is centered about the carrier opening 210, 810, 910. The specimen 100 is positioned onto surfaces 300, 300a and may be wedged or placed against the edges 310a, 310b for additional support. In FIG. 11, the top of the EXLO specimen 100 is manipulated in an upright orientation 410 to a position where it extends beyond the facing edge 330 of the carrier (200, 800, or 900). Glue or epoxy 420 may be used to adhere the specimen 100 to the carrier 200 and the grid carrier opening (210, 810, or 910).

Figure 12:
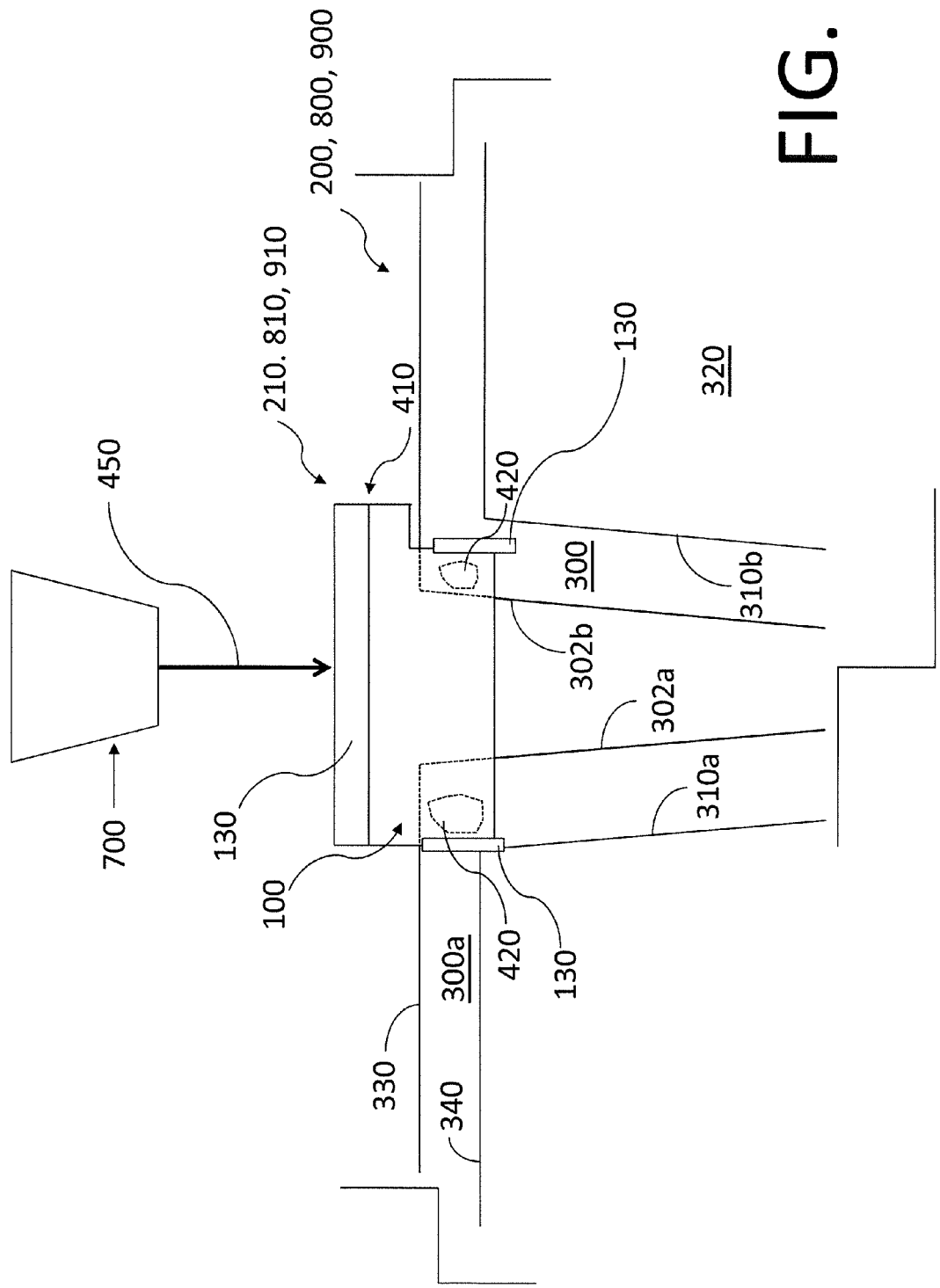
FIG. 12 shows a plan view of the specimen support area of FIG. 4 with the EXLO specimen of FIG. 1 mounted thereon in an upright orientation above a facing surface of the grid just prior to milling.

FIG. 12 shows an EXLO specimen in an upright orientation after manipulation to a low profile grid carrier apparatus. The specimen may be further milled at this point using a focused ion beam tool 700 projected along path 450. FIG. 12 further shows a glued 420 upright oriented EXLO specimen (100, 410) after manipulation onto a carrier (200, 800, or 900) and the carrier opening (210, 810, 910). The specimen may be directly analyzed at this point or may be put back into a FIB/SEM or similar where an additional layer 130 may be deposited on one or more sides to further secure and protect the specimen 100.

Figure 13:
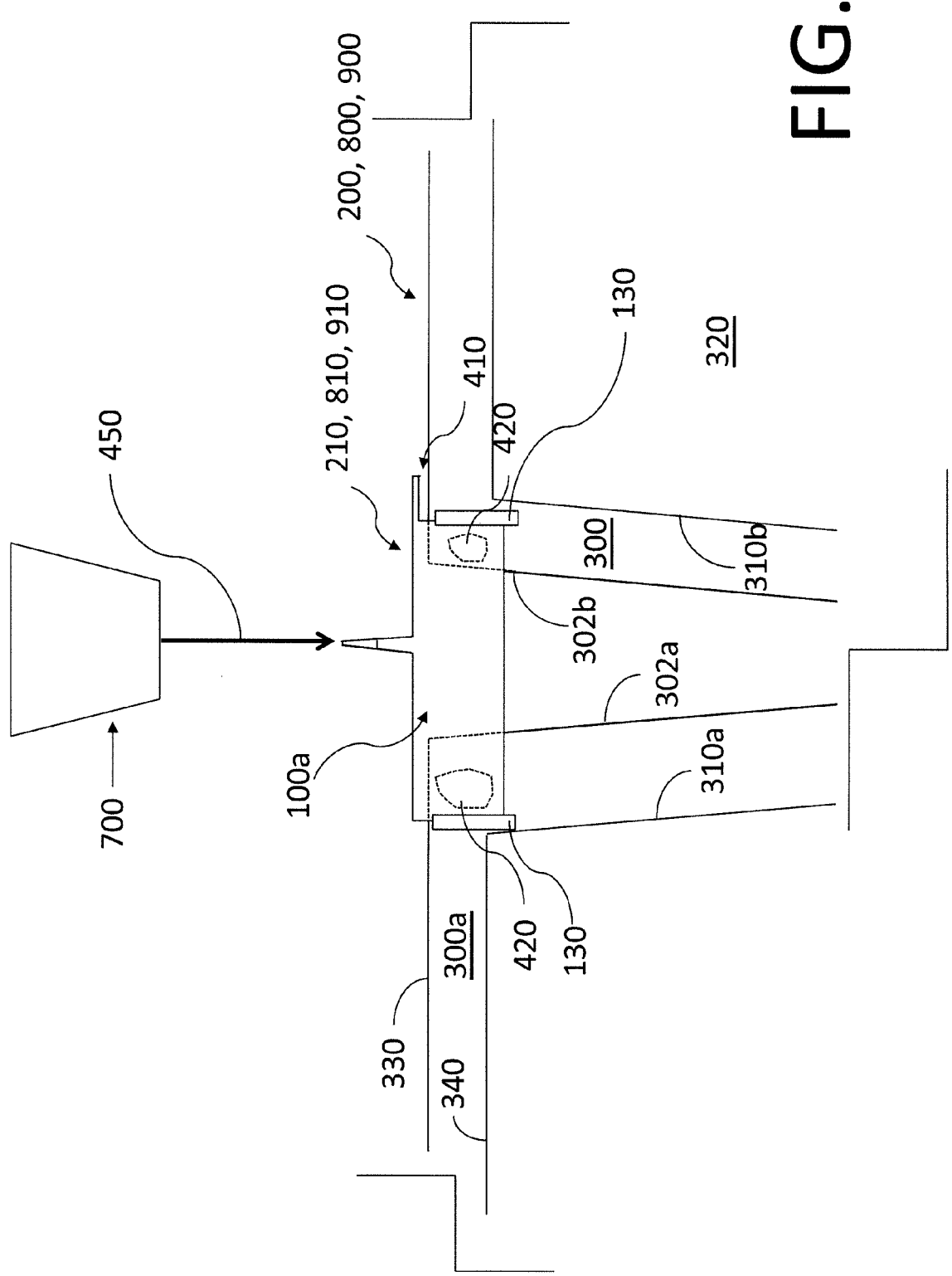
FIG. 13 shows a plan view of the specimen and specimen carrier of FIG. 12 after the mounted specimen has been milled.

As shown in FIG. 13, the specimen may be further thinned by a FIB or laser tool 700 along path 450 to yield thinned needle shaped specimen 100a or may be processed alternatively by a thinning beam (e.g., FIB or laser) and an imaging beam (e.g., FIB 450, SEM, TEM etc. (not shown)) for 3D tomography. If the specimen is manipulated onto a low profile carrier (800 or 900) then the specimen may be FIB or laser processed to a sharp needle which may be suitable for e.g., electron tomography or atom probe tomography analysis of the specimen.

Figure 14:
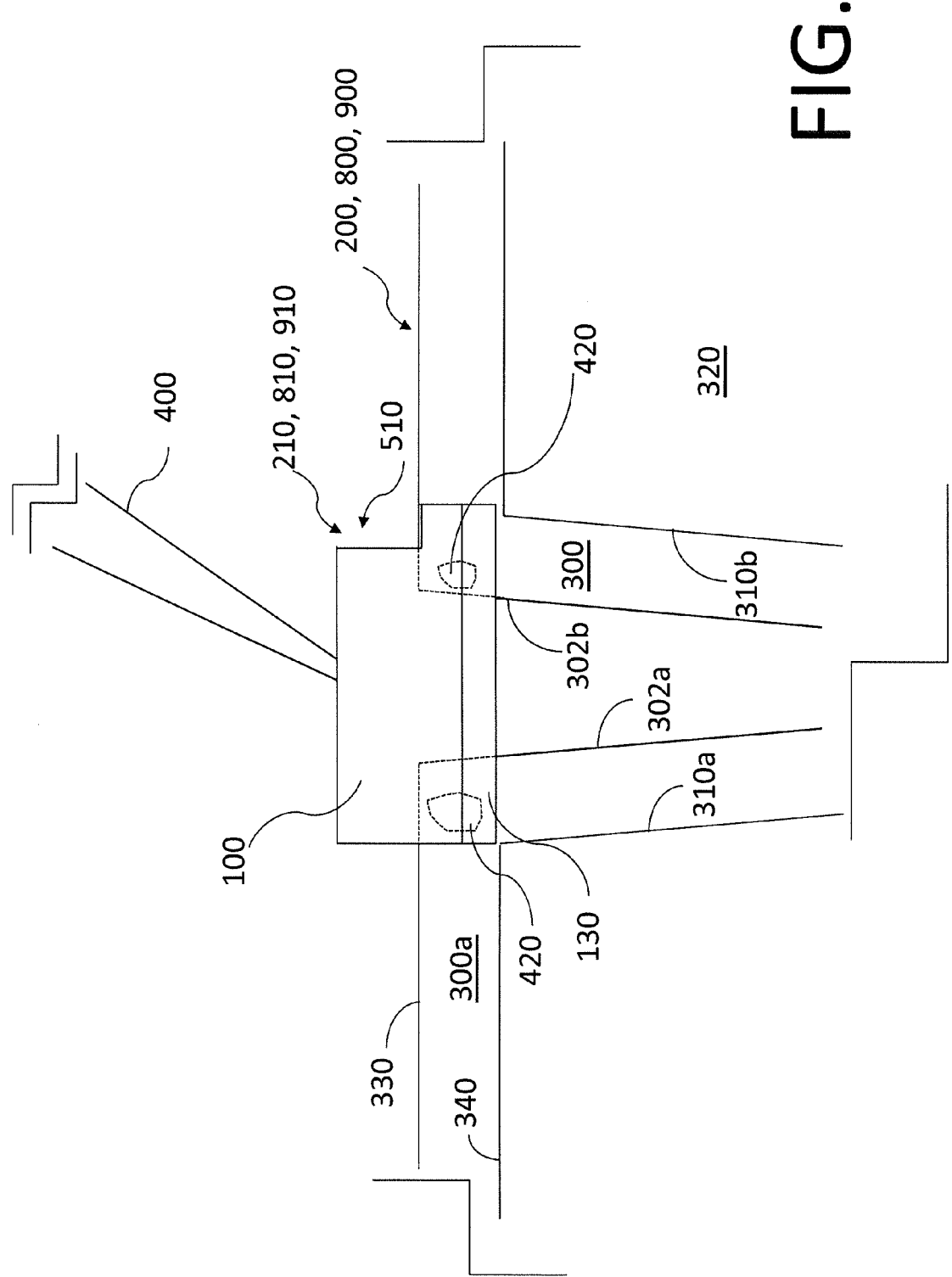
FIG. 14 shows a plan view of the specimen support area of FIG. 4 with an EXLO specimen manipulated to a backside orientation above a facing surface of the grid.

FIG. 14 shows the manipulation of an EXLO specimen in a backside orientation onto a low profile grid carrier apparatus. A manipulator 400 operates to position an EXLO specimen 100 onto a carrier apparatus (200, 800, or 900) whose region of interested is centered about the carrier opening 210, 810, or 910. The specimen 100 is positioned onto surfaces 300 and may be wedged or placed against the sidewalls 310a, 310b spanning surface 300 for additional support. In FIG. 14, the top of the EXLO specimen 100 extends over the edge 330 of the carrier (200, 800, or 900) and is manipulated into a backside orientation 510. The use of glue or epoxy 420 may be used to adhere the specimen 100 to the carrier (200, 800, or 900) and the grid carrier opening (210, 810, or 910).

Figure 15:
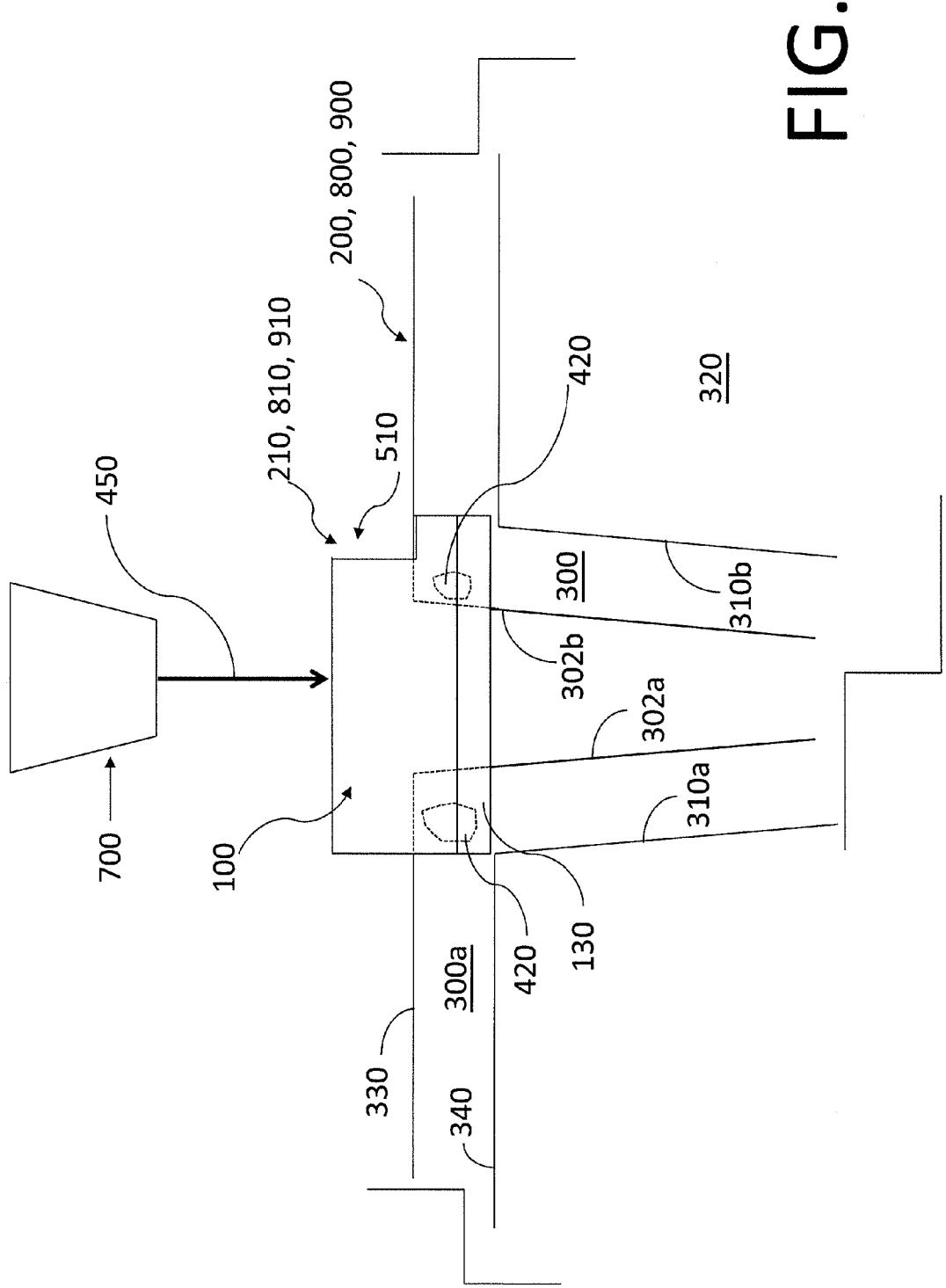
FIG. 15 shows a plan view of the specimen support area of FIG. 4 with an EXLO specimen mounted thereon in a backside orientation above a facing surface of the grid just prior to milling.

FIG. 15 shows an EXLO specimen in a backside orientation after manipulation to a low profile grid carrier apparatus where a portion of the backside of the specimen extends over the surface of the grid. The figure shows a glued 420 backside oriented EXLO specimen (100, 410) after manipulation onto a carrier (200, 800, or 900) and the carrier opening (210, 810, or 910). The specimen may be directly analyzed at this point or may be put back into a FIB/SEM or similar where an additional layer 130 may be deposited on one or more sides to further secure and protect the specimen 100. The specimen may be further thinned by a FIB or laser 700 along path 450.

Figure 16:
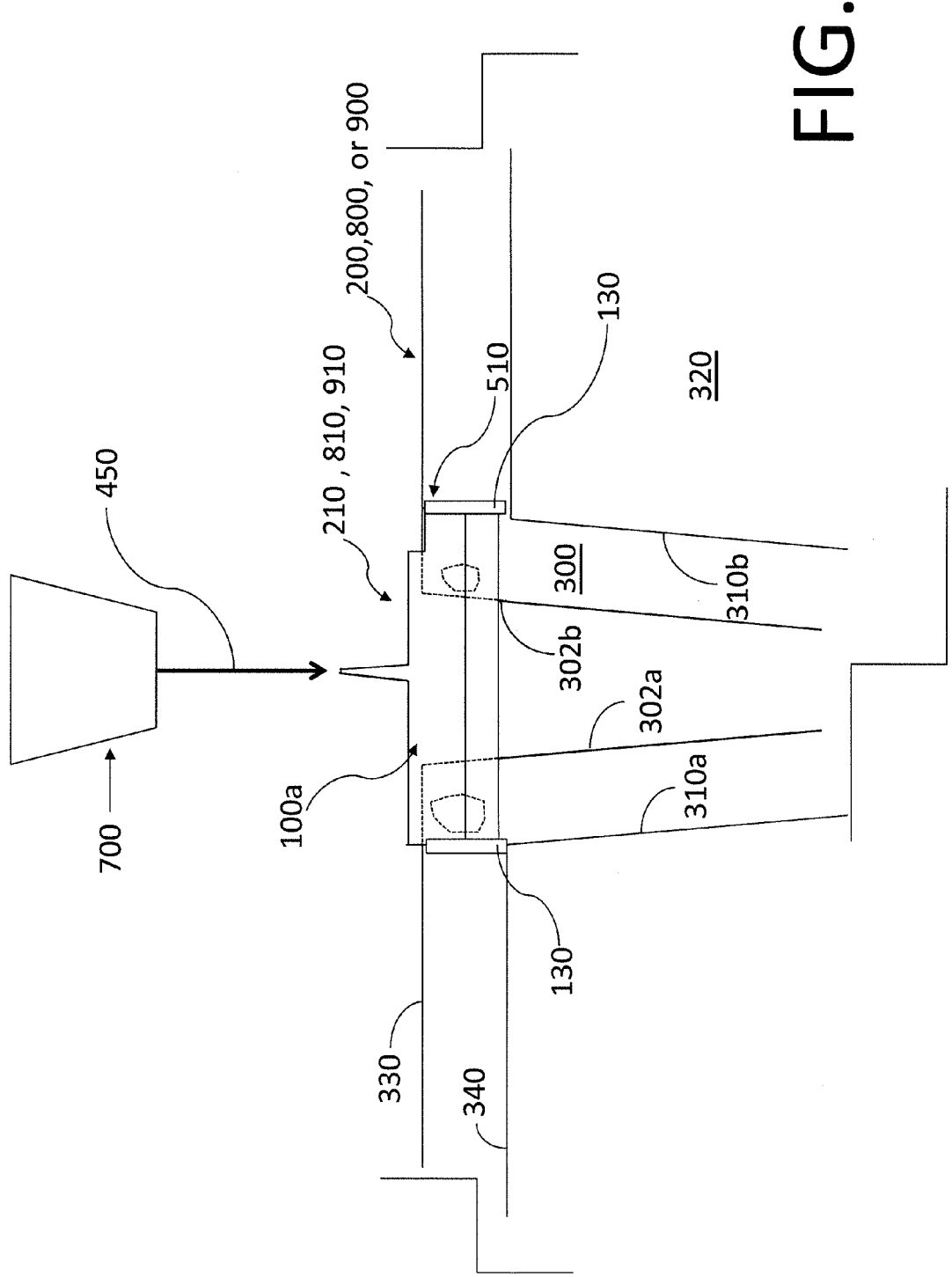
FIG. 16 shows a plan view of the specimen and specimen carrier of FIG. 14 after the mounted specimen has been milled.

As shown in FIG. 16, the specimen may be further thinned by a FIB or laser 700 along path 450 to produce a thinned needle shaped specimen 100a which may be suitable for e.g., electron tomography or atom probe tomography analysis of the specimen. Alternatively, the specimen may be processed alternatively by a thinning beam (e.g., FIB or laser 450) and an imaging beam (e.g., FIB 450, SEM, TEM etc. (not shown)) for 3D tomography.

Figure 17:
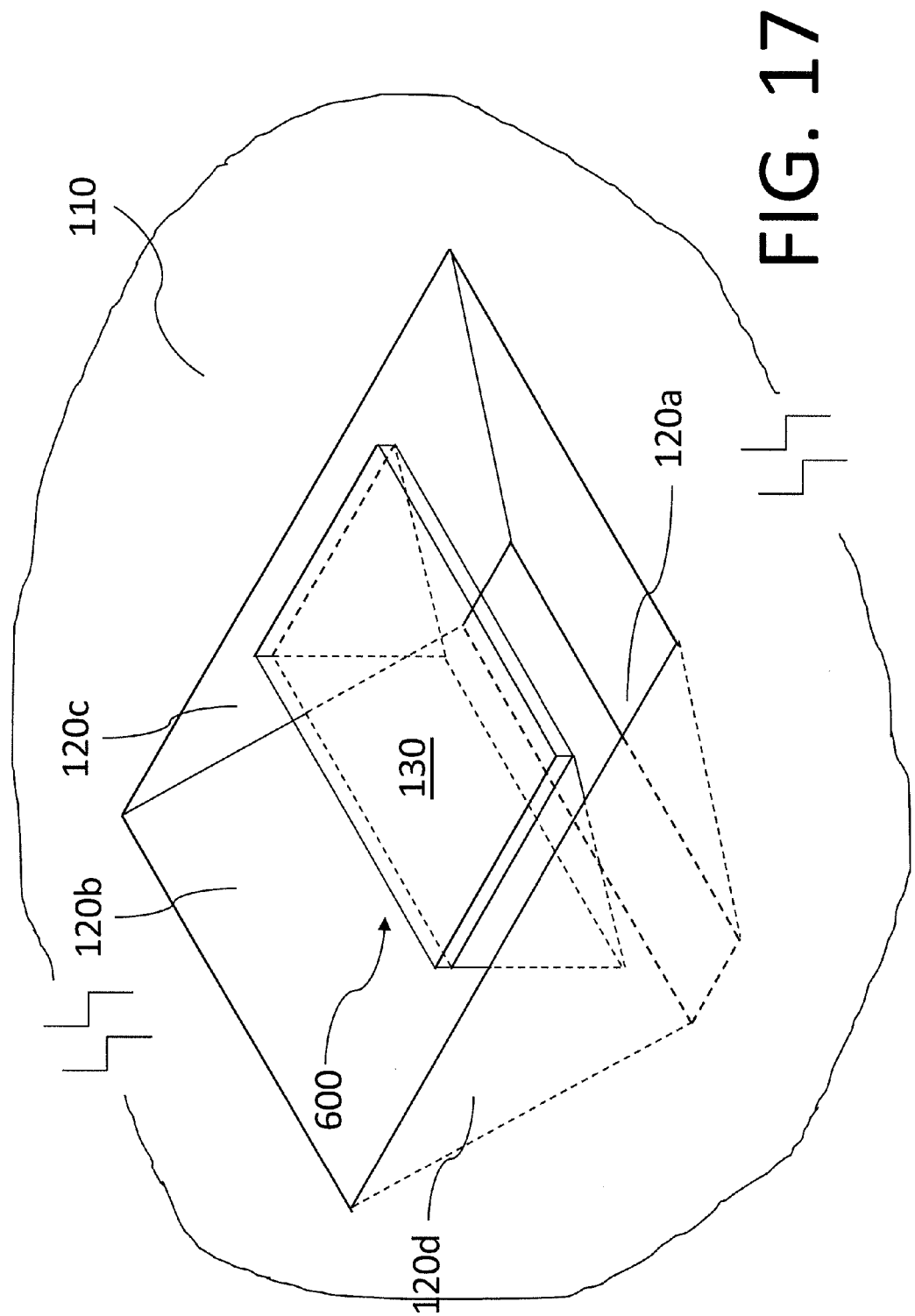
FIG. 17 is a perspective view of a specimen taken from a sample to be analyzed where the specimen is configured in a wedge shape to uniquely identify an orientation of the specimen.

FIG. 17 shows an EXLO FIB milled specimen milled into a wedge shape conventionally used for plan view specimen analysis where the area of interest would be parallel to the original target surface 110. The figure shows a wedge-shaped plan view EXLO specimen 600 FIB milled from the target surface 110. The EXLO specimen 600 sits inside of FIB milled trenches 120a, 120b, 120c, and 120d. The specimen 600 may be denoted by a protective layer 130 which may be deposited inside of a dual platform (FIB/SEM) instrument. This layer 130 may be platinum, carbon, tungsten or similar and is used to denote the region of interest and protect the underlying region from spurious milling. The deposited layer may also be used as a marker to orient the specimen.

Figure 18:
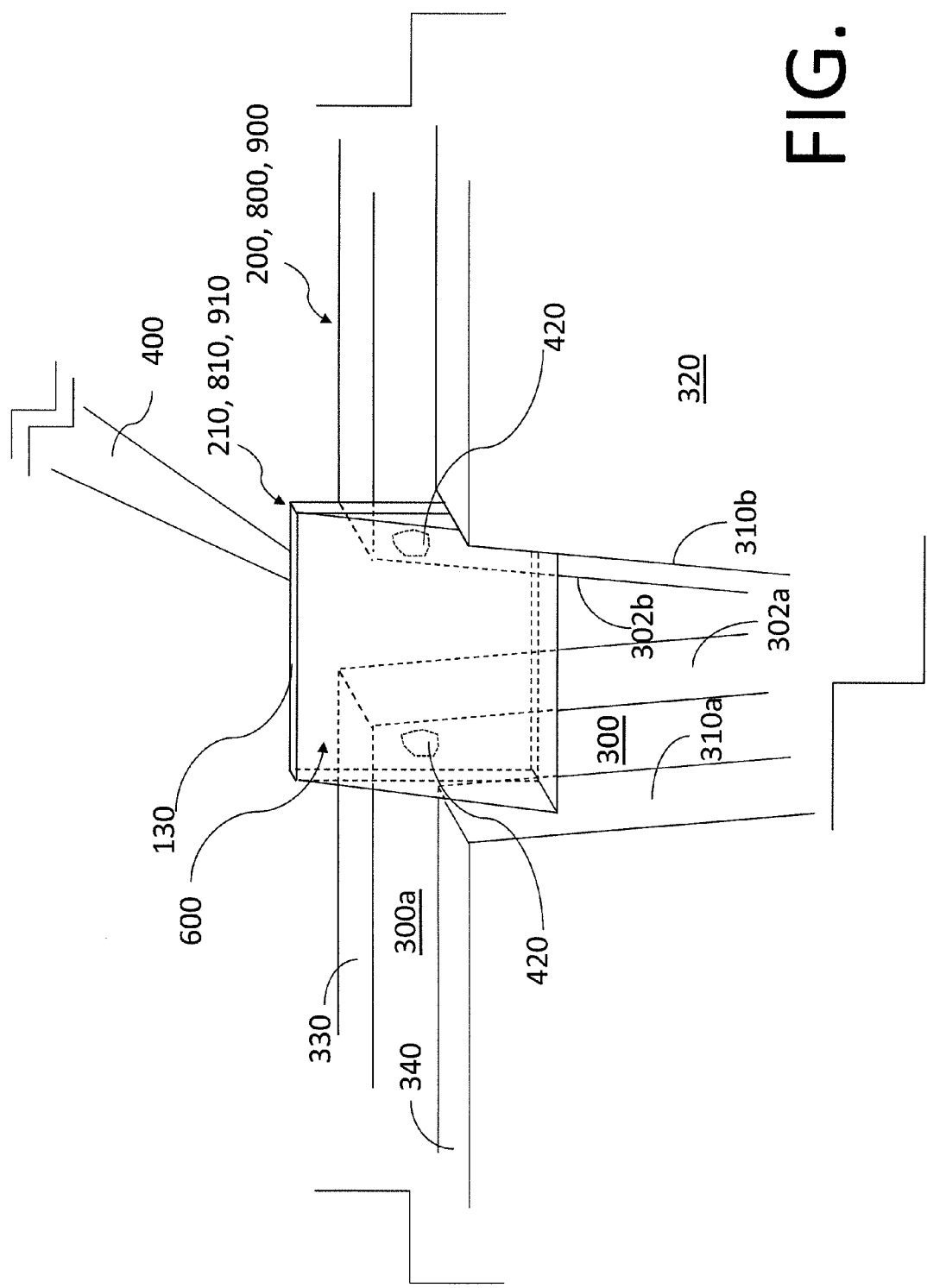
FIG. 18 shows a plan view of the specimen support area of FIG. 4 with the EXLO specimen of FIG. 17 manipulated to an upright orientation above a facing surface of the grid.

FIG. 18 shows the manipulation, using an ex-situ manipulator 400, of an EXLO wedge-shaped specimen 600 in a low profile grid carrier orientation for plan view analysis. Specimen 600 can also be manipulated to a grid such as in FIG. 2 (not shown). The figure further shows the manipulation of the wedge-shaped plan view EXLO specimen 600 onto a newly designed grid carrier (200, 800, or 900) whose region of interest is centered about the carrier opening (210, 810 or 910). The specimen 600 is positioned onto recessed mounting surfaces 300, 300a and may be wedged or placed against the sidewalls 310a, 310b of the first opening 210a for additional support. Glue, epoxy, or adhesive 420 may be used to adhere the specimen 600 to the carrier (200, 800, or 900) and the grid carrier opening (210, 810, or 910) onto surfaces 300, 300a. The specimen 600 may be manipulated either above surface 330 as shown in FIG. 18 if tomographic analysis is necessary or below surface 330 for conventional analysis (not shown).

Figure 19:
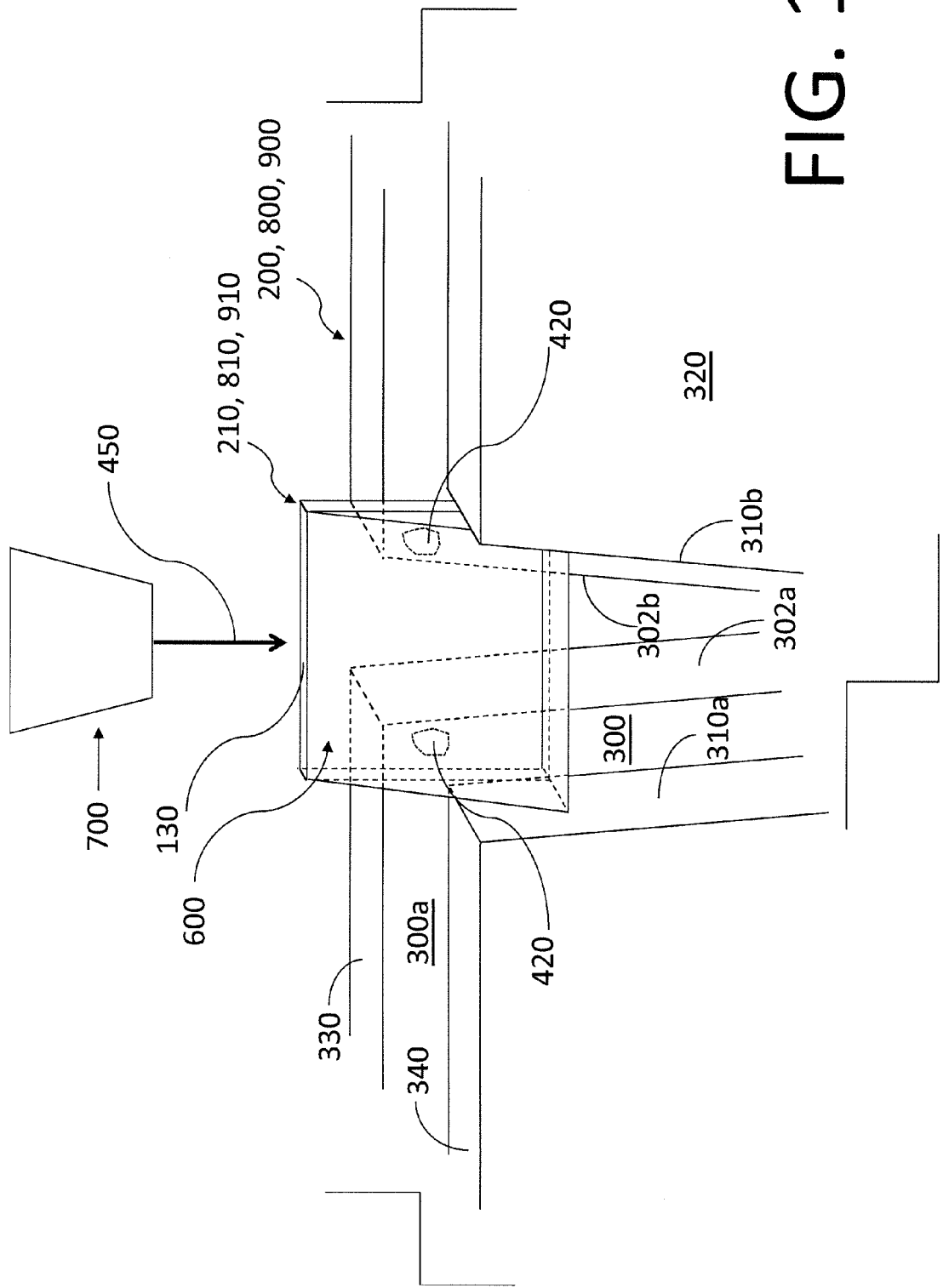
FIG. 19 shows a plan view of the specimen support area of FIG. 4 with the EXLO specimen of FIG. 17 mounted thereon in an upright orientation above a facing surface of the grid just prior to milling.

FIG. 19 shows an EXLO wedge-shaped specimen in a low profile grid carrier orientation after manipulation, where the specimen 600 may be FIB processed to reveal a surface parallel to the original target surface. The figure further shows a glued 420 wedge-shaped plan view EXLO specimen 600 after manipulation onto the carrier (200, 800, or 900) and the carrier opening (210, 810, or 910) onto surfaces 300, 300a. The specimen may be directly analyzed at this point or may be put back into a FIB/SEM or similar where an additional layer 130 may be deposited on one or more sides to further secure and protect the specimen 600. The specimen may be further thinned by a FIB or laser for plan view analysis or may be processed alternatively by a thinning beam (e.g., FIB or laser) and an imaging beam (e.g., FIB, SEM, TEM etc.) for 3D tomography. At this point a plan view needle shaped specimen (similar to the one shown in FIG. 16) may be FIB milled or laser processed for e.g., electron tomography or atom probe tomography.

Having described and illustrated the principles of the invention in a preferred embodiment thereof, it should be apparent that the invention can be modified in arrangement and detail without departing from such principles. I claim all modifications and variation coming within the spirit and scope of the invention.

What is claimed is:

1. A method for mounting a specimen on a specimen carrier for milling in an ex-situ lift-out (EXLO) milling process where "cross-section" specimens, plan view specimens, bulk specimens may be lifted-out for analysis, the method comprising:
positioning the specimen on a recessed surface within a specimen carrier top surface ex-situ so that a region to be milled is centered about a carrier opening formed through the specimen carrier;
wedging peripheral edges of the specimen against inwardly sloping side walls framing the recessed surface; and
mounting the specimen on the specimen carrier so that a path of a milling beam intersects the region to be milled and carrier opening.

2. The method of claim 1, wherein the specimen carrier is rotated to present a backside of the specimen positioned on the recessed surface to the milling beam.

3. The method of claim 1, wherein the specimen is rotated on the specimen carrier to present a backside of the specimen positioned on the recessed surface to the milling beam.

4. The method of claim 1, wherein the specimen is configured with an asymmetry cut so that an orientation of the specimen can be determined when the specimen is mounted in the specimen carrier.

5. The method of claim 4, wherein the asymmetry is defined by an asymmetric cut formed on a single side of the specimen.

6. The method of claim 4, wherein the asymmetric cut results in the specimen having a wedge shape.

7. The method of claim 6, wherein the wedge shape has profile with a right angle.

8. The method of claim 1, wherein the step of mounting the specimen on the carrier includes interposing a glue, adhesive or epoxy between the specimen and the recessed surface on the carrier.

9. The method of claim 4 wherein the asymmetry of the specimen is defined by a protective deposition layer.

10. A method for mounting a specimen on a specimen carrier for milling in an ex-situ lift-out (EXLO) milling process where "cross-section" specimens, plan view specimens, bulk specimens may be lifted-out for analysis, the method comprising:
positioning the specimen on a recessed surface within a specimen carrier top surface ex-situ so that a region to be milled is centered about a carrier opening formed through the specimen carrier; and
mounting the specimen on the specimen carrier so that a path of a milling beam intersects the region to be milled and carrier opening,
whereby mounting the specimen on the specimen carrier includes adhering peripheral edges of the specimen to the recessed surface on either side of the carrier opening so that a middle portion of the specimen spans across the carrier opening on the recessed surface.

11. The method of claim 10, wherein the specimen carrier is rotated to present a backside of the specimen positioned on the recessed surface to the milling beam.

12. The method of claim 10, further including the step of rotating the specimen carrier to present a backside of the specimen positioned on the recessed surface to the milling beam.

13. The method of claim 10, further including the step of forming an asymmetry cut on the specimen so that an orientation of the specimen can be determined when the specimen is mounted in the specimen carrier.

14. The method of claim 13, wherein the asymmetry is defined by an asymmetric cut formed on a single side of the specimen.

15. The method of claim 13, wherein the asymmetry of the specimen is defined by a protective deposition layer.

16. The method of claim 13, wherein the asymmetric cut results in the specimen having a wedge shape.

17. The method of claim 16, wherein the wedge shape has profile with a right angle.

18. The method of claim 10, wherein the step of adhering the specimen on the carrier includes interposing a glue, adhesive or epoxy between the specimen and the recessed surface on the carrier.

19. The method of claim 10, wherein the step of adhering the specimen on the carrier includes adhering solely via large surface tension forces.

\* \* \* \* \*